US012148191B2

(12) United States Patent
Ma et al.

(10) Patent No.: US 12,148,191 B2
(45) Date of Patent: Nov. 19, 2024

(54) IMAGING SYSTEMS AND METHODS

(71) Applicant: SHANGHAI UNITED IMAGING HEALTHCARE CO., LTD., Shanghai (CN)

(72) Inventors: Yan'ge Ma, Shanghai (CN); Le Yang, Shanghai (CN); Juan Feng, Shanghai (CN); Jie Niu, Shanghai (CN); Kai Cui, Shanghai (CN); Wenri Zhang, Shanghai (CN); Na Zhang, Shanghai (CN); Peng Yao, Shanghai (CN); Yang Hu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 92 days.

(21) Appl. No.: 17/810,309

(22) Filed: Jun. 30, 2022

(65) Prior Publication Data
US 2022/0353409 A1 Nov. 3, 2022

Related U.S. Application Data

(63) Continuation of application No. PCT/CN2020/140733, filed on Dec. 29, 2020.

(30) Foreign Application Priority Data

Dec. 31, 2019 (CN) .......................... 201911410616.5
Dec. 31, 2019 (CN) .......................... 201911417920.2

(51) Int. Cl.
G06V 10/25 (2022.01)
A61B 6/00 (2024.01)
(Continued)

(52) U.S. Cl.
CPC ................ *G06V 10/25* (2022.01); *G06T 7/74* (2017.01); *H04N 23/64* (2023.01);
(Continued)

(58) Field of Classification Search
CPC ...... G06V 10/25; G06V 2201/03; G06T 7/74; G06T 2207/30196; H04N 23/64;
(Continued)

(56) References Cited

U.S. PATENT DOCUMENTS

2004/0101180 A1* 5/2004 Doi ....................... G06T 7/0012
382/128
2007/0238963 A1 10/2007 Kaminaga et al.
(Continued)

FOREIGN PATENT DOCUMENTS

CN 102988075 A 3/2013
CN 106303203 A 1/2017
(Continued)

OTHER PUBLICATIONS

The Extended European Search Report in European Application No. 20910902.4 mailed on Dec. 9, 2022, 7 pages.
(Continued)

Primary Examiner — Tung T Vo
(74) Attorney, Agent, or Firm — METIS IP LLC

(57) ABSTRACT

The present disclosure provides a method for automated image acquisition and imaging processing. The method may include obtaining imaging information of an object. The method may include determining, based on the imaging information, at least target device positioning information of an imaging device. The method may include causing, based on the target device positioning information of the imaging device, the imaging device to be positioned to perform the image acquisition. The method may include providing, based on the inspection information, guidance information,
(Continued)

the guidance information being configured to guide positioning of the object. The method may also include obtaining a target image from an imaging operation by the imaging device. Further, the method may include determining a target image processing algorithm of a medical image.

20 Claims, 10 Drawing Sheets

(51) Int. Cl.
    *G06T 7/73*         (2017.01)
    *H04N 23/60*       (2023.01)
    *H04N 23/695*     (2023.01)

(52) U.S. Cl.
    CPC ............ *H04N 23/695* (2023.01); *A61B 6/542* (2013.01); *G06T 2207/30196* (2013.01)

(58) Field of Classification Search
    CPC ........ H04N 23/695; A61B 6/542; A61B 6/46; A61B 6/467; A61B 6/469; A61B 6/545; G16H 15/00; G16H 30/20; G16H 30/40; G16H 40/63; G16H 40/67
    USPC .......................................................... 348/77
    See application file for complete search history.

(56) References Cited

U.S. PATENT DOCUMENTS

| | | | |
|---|---|---|---|
| 2009/0116710 A1 | 5/2009 | Futami et al. | |
| 2011/0052034 A1 | 3/2011 | Watanabe | |
| 2013/0188852 A1 | 7/2013 | Bakai et al. | |
| 2014/0348401 A1 | 11/2014 | Xu et al. | |
| 2014/0378816 A1* | 12/2014 | Oh | A61B 6/54 |
| | | | 600/407 |
| 2015/0051489 A1* | 2/2015 | Caluser | A61B 8/5207 |
| | | | 600/440 |
| 2016/0029986 A1 | 2/2016 | Nishii et al. | |
| 2016/0166329 A1* | 6/2016 | Langan | A61B 6/4014 |
| | | | 600/424 |
| 2018/0140270 A1 | 5/2018 | Profio et al. | |
| 2018/0253842 A1 | 9/2018 | Allmendinger et al. | |
| 2019/0059829 A1* | 2/2019 | Han | A61B 6/469 |
| 2020/0020097 A1* | 1/2020 | Do | G06F 18/2413 |
| 2021/0000446 A1* | 1/2021 | Toporek | A61B 8/4245 |
| 2021/0015453 A1* | 1/2021 | Toporek | G16H 30/40 |
| 2021/0038321 A1* | 2/2021 | Toporek | G06V 10/764 |

FOREIGN PATENT DOCUMENTS

| | | |
|---|---|---|
| CN | 106361364 A | 2/2017 |
| CN | 107085860 A | 8/2017 |
| CN | 206907026 U | 1/2018 |
| CN | 109241908 A | 1/2019 |
| CN | 109276248 A | 1/2019 |
| CN | 110192891 A | 9/2019 |
| CN | 110266951 A | 9/2019 |
| CN | 110292723 A | 10/2019 |
| CN | 110353711 A | 10/2019 |
| CN | 110458837 A | 11/2019 |
| CN | 111178297 A | 5/2020 |
| JP | 2003275194 A | 9/2003 |
| JP | 2015173667 A | 10/2015 |
| WO | 2019200351 A1 | 10/2019 |

OTHER PUBLICATIONS

International Search Report in PCT/CN2020/140733 mailed on Mar. 25, 2021, 5 pages.
Written Opinion in PCT/CN2020/140733 mailed on Mar. 25, 2021, 6 pages.

* cited by examiner

IMAGING SYSTEMS AND METHODS

CROSS-REFERENCE TO RELATED APPLICATION

The present application is a continuation of International Application No. PCT/CN2020/140733, filed on Dec. 29, 2020, which designates the United States of America and claims priority of Chinese Patent Application No. 201911417920.2 filed on Dec. 31, 2019 and Chinese Patent Application No. 201911410616.5 filed on Dec. 31, 2019, the contents of each of which are hereby incorporated by reference.

TECHNICAL FIELD

The present disclosure relates to the field of medical imaging, and more particularly relates to systems and methods for image acquisition and image processing.

BACKGROUND

Medical imaging technique is widely used in medical examinations and diagnoses in recent years. For example, with the development of X-ray imaging technology, a digital radiography (DR) system has become more and more important in, such as, breast tomosynthesis, chest examination, or the like.

SUMMARY

In a first aspect of the present disclosure, a method for automated image acquisition is provided. The method may be implemented on at least one computing device, each of which may include at least one processor and a storage device. The method may include obtaining imaging information of an object. The imaging information may include identity information and inspection information. The method may include determining, based on the identity information and the inspection information, at least target device positioning information of an imaging device. The method may also include causing, based on the target device positioning information of the imaging device, the imaging device to be positioned to perform the image acquisition. The method may include providing, based on the inspection information, guidance information. The guidance information may be configured to guide positioning of the object. Further, the method may include obtaining a target image from an imaging operation by the imaging device.

In some embodiments, the determining, based on the identity information and the inspection information, at least target device positioning information of an imaging device may include determining, based on the identity information and the inspection information, the target device positioning information and target imaging information of the imaging device. The target imaging information may include target exposure information. In some embodiments, the obtaining a target image from an imaging operation of the imaging device may include, in response to completing the positioning of the object, causing the imaging device to perform an exposure operation according to the target exposure information.

In some embodiments, the providing, based on the inspection information, guidance information may include determining, based on the inspection information, target patient positioning information of the object; and determining, based on the target patient positioning information of the object, the guidance information.

In some embodiments, the determining, based on the target patient positioning information of the object, the guidance information may include obtaining current patient positioning information of the object; comparing the current patient positioning information of the object with the target patient positioning information of the object; and determining, based on a comparison result between the current patient positioning information of the object and the target patient positioning information of the object, the guidance information.

In some embodiments, the determining, based on the target patient positioning information of the object, the guidance information may further include obtaining current patient positioning information of the object; generating, based on the target patient positioning information of the object, a positioning reference image; comparing the current patient positioning information of the object with the positioning reference image; and determining, based on a comparison result between the current patient positioning information of the object and the positioning reference image, the guidance information.

In some embodiments, the causing, based on the target device positioning information of the imaging device, the imaging device to be positioned to perform the image acquisition may include generating, based on the target device positioning information of the imaging device, a control instruction of the imaging device; and causing the imaging device to be positioned according to the control instruction.

In some embodiments, the method may further include performing a feature recognition on the target image to generate a feature recognition result of the object; generating, based on the feature recognition result, a result report; and transmitting the result report to one or more target client terminals.

In a second aspect of the present disclosure, a system for automated image acquisition is provided. The system may include an information obtaining module, a device positioning module, a guidance information providing module, and an image obtaining module. The information obtaining module may be configured to obtain imaging information of an object. The imaging information may include identity information and inspection information. The device positioning module may be configured to determine, based on the identity information and the inspection information, at least target device positioning information of an imaging device, and cause, based on the target device positioning information of the imaging device, the imaging device to be positioned to perform the image acquisition. The guidance information providing module may be configured to provide, based on the inspection information, guidance information. The guidance information may be configured to guide positioning of the object. The image obtaining module may be configured to obtain a target image from an imaging operation by the imaging device.

In a third aspect of the present disclosure, a method for image processing is provided. The method may be implemented on at least one computing device, each of which may include at least one processor and a storage device. The method may include obtaining, using an imaging device, a medical image of an object acquired according to a current imaging protocol. The medical image may include a representation of a region of interest of the object. The method may include determining whether the medical image is compatible with the current imaging protocol. In response to determining whether the medical image is compatible with the current imaging protocol, the method may further include determining a target image processing algorithm of the medical image.

In some embodiments, the determining, in response to determining whether the medical image is compatible with the current imaging protocol, a target image processing algorithm of the medical image may include, in response to determining that the medical image is incompatible with the current imaging protocol, determining the target image processing algorithm by adjusting, based on the medical image, a current image processing algorithm that relates to the current imaging protocol.

In some embodiments, the determining, in response to determining whether the medical image is compatible with the current imaging protocol, a target image processing algorithm of the medical image may include, in response to determining that the medical image is compatible with the current imaging protocol, designating a current image processing algorithm that relates to the current imaging protocol as the target image processing algorithm.

In some embodiments, the determining whether the medical image is compatible with the current imaging protocol may include determining, based on the medical image, the region of interest of the object; and determining whether the region of interest of the object is compatible with the current imaging protocol.

In some embodiments, the determining, based on the medical image, the region of interest of the object may include performing a segmentation operation on the medical image to determine a plurality of regions; and determining, based on the plurality of regions, the region of interest of the object.

In some embodiments, the determining, based on the plurality of regions, the region of interest of the object may include determining at least one of a ratio of bone tissue or a ratio of soft tissue of at least one of the plurality of regions; and determining, based on the at least one ratio, the region of interest of the object.

In some embodiments, the determining at least one of a ratio of bone tissue or a ratio of soft tissue of at least one of the plurality of regions may include obtaining grayscale data of at least one pixel of the at least one region and an imaging parameter of the current imaging protocol, and determining, based on the grayscale data of the at least one pixel and the imaging parameter, the at least one ratio of the at least one region.

In some embodiments, the imaging parameter may include at least one of an imaging dose employed in acquiring the medical image, a distance from a tube to a detector of the imaging device, or grid information of the imaging device.

In some embodiments, the method may further include obtaining a preliminary image of a current posture of the object; determining whether the preliminary image is compatible with a pending imaging protocol; and determining a prompt in response to determining whether the preliminary image is compatible with the current imaging protocol.

In some embodiments, the determining a prompt in response to determining whether the preliminary image is compatible with the current imaging protocol may include, in response to determining that the preliminary image is incompatible with the current imaging protocol, the prompt including a request for a protocol adjustment or a request for a position adjustment.

In some embodiments, the determining whether the medical image is compatible with the current imaging protocol may include inputting the medical image and the current imaging protocol into a compatibility verification model; and determining, based on an output of the compatibility verification model, whether the medical image is compatible with the current imaging protocol.

In some embodiments, the preliminary image may include an optical image or an infrared image.

In a fourth aspect of the present disclosure, a system for image processing is provided. The system may include an obtaining module, a determination module, and a processing module. The obtaining module may be configured to obtain, using an imaging device, a medical image of an object acquired according to a current imaging protocol. The medical image may include a representation of a region of interest of the object. The determination module may be configured to determine whether the medical image is compatible with the current imaging protocol. The processing module may be configured to determine a target image processing algorithm of the medical image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Figure 2:
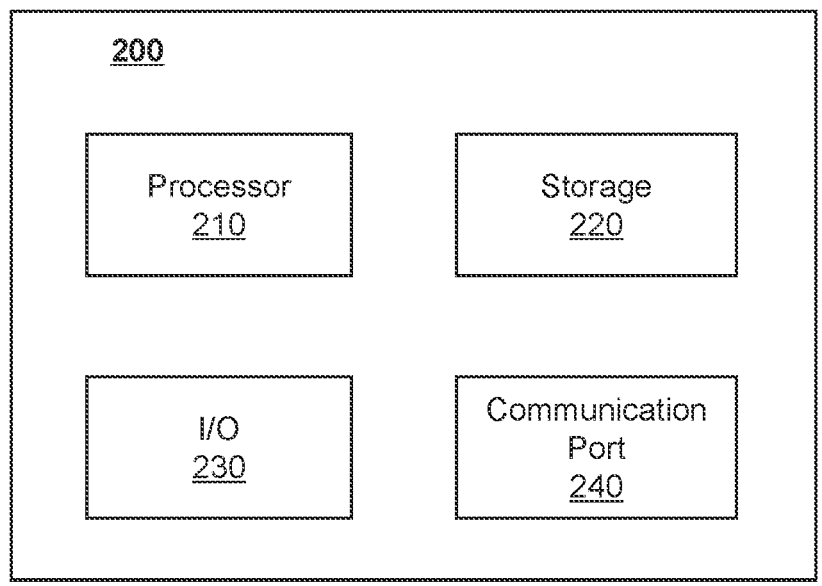
FIG. 2 is a schematic diagram illustrating an exemplary computing device on which at least a portion of the imaging system 100 can be implemented, according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., a processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on an object's body, since the image may indicate the actual location of a certain anatomical structure existing in or on the object's body. The term "an image of an object" may be referred to as the object for brevity. Segmentation of an image of an object may be referred to as segmentation of the object. It will be understood that the term "imaging operation" and "exposure operation" may be used interchangeably to obtain an image in the present disclosure. Similarly, the term "imaging information" and "exposure information," and the term "imaging dose" and "exposure dose," and the term "imaging parameter" and "exposure parameter" may be used interchangeably.

As used herein, a representation of an object (e.g., a patient, or a portion thereof) in an image may be referred to as the object for brevity. For instance, a representation of an organ or tissue (e.g., the heart, the liver, a lung, etc., of a patient) in an image may be referred to as the organ or tissue for brevity. As used herein, an operation on a representation of an object in an image may be referred to as an operation on the object for brevity. For instance, a segmentation of a portion of an image including a representation of an organ or tissue (e.g., the heart, the liver, a lung, etc., of a patient) from the image may be referred to as a segmentation of the organ or tissue for brevity.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Figure 1:
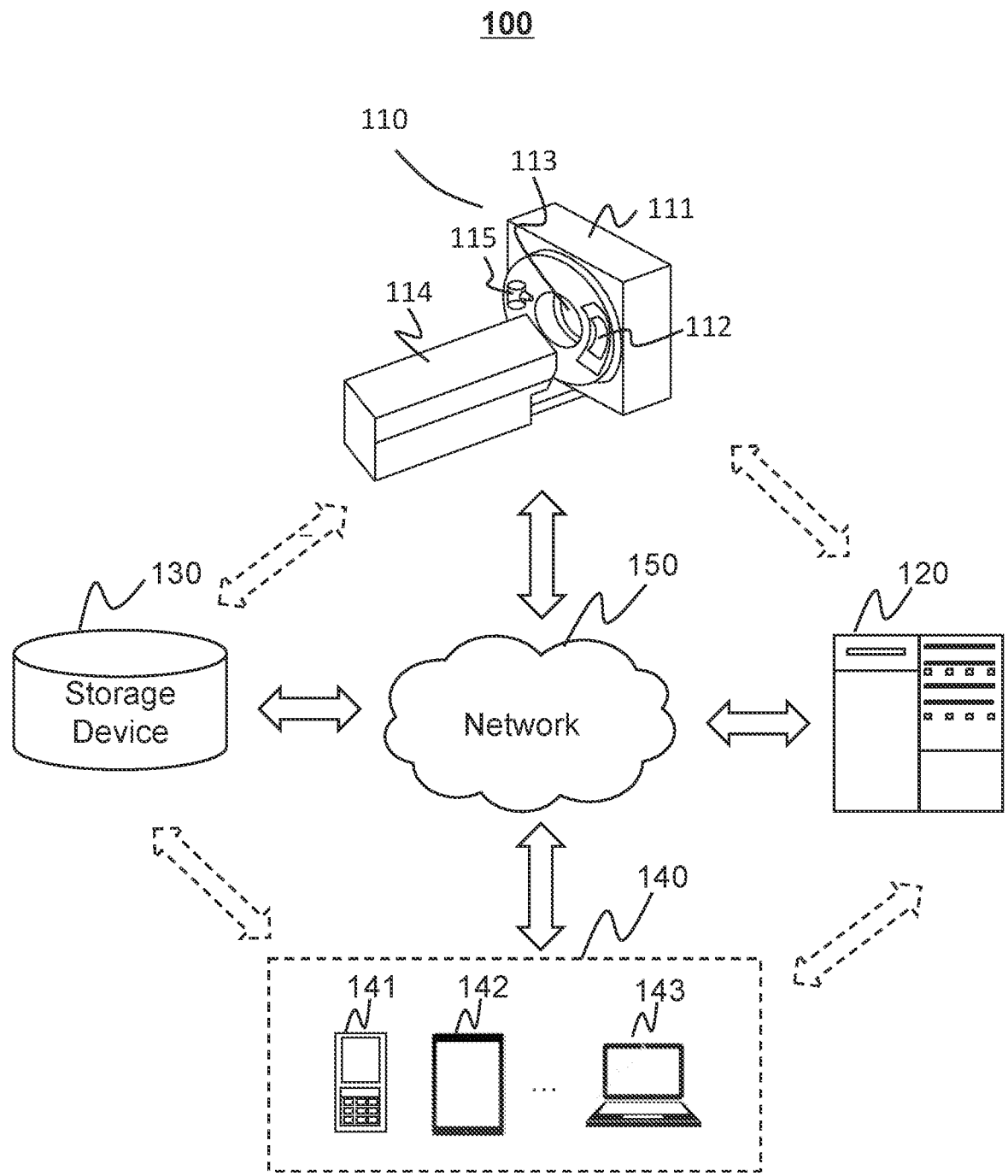
FIG. 1 is a schematic diagram illustrating an exemplary imaging system according to some embodiments of the present disclosure.

FIG. 1 is a schematic diagram illustrating an exemplary imaging system 100 according to some embodiments of the present disclosure. As shown, the imaging system 100 may include an imaging device 110, a processing device 120, a storage device 130, one or more terminals 140, and a network 150. In some embodiments, the imaging device 110, the processing device 120, the storage device 130, and/or the terminal(s) 140 may be connected to and/or communicate with each other via a wireless connection, a wired connection, or a combination thereof. The connection between the components of the imaging system 100 may be variable. Merely by way of example, the imaging device 110 may be connected to the processing device 120 through the network 150 or directly. As a further example, the storage device 130 may be connected to the processing device 120 through the network 150 or directly.

The imaging device 110 may generate or provide image data related to an object via scanning the object. For illustration purposes, image data of an object acquired using the imaging device 110 is referred to as medical image data or image data. In some embodiments, the object may include a biological object and/or a non-biological object. For example, the object may include a specific portion of a body, such as the head, the thorax, the abdomen, or the like, or a combination thereof. As another example, the object may be a man-made composition of organic and/or inorganic matters that are with or without life. In some embodiments, the imaging system 100 may include modules and/or components for performing imaging and/or related analysis. In some embodiments, the medical image data relating to the object may include projection data, one or more images of the object, etc. The projection data may include raw data generated by the imaging device 110 by scanning the object and/or data generated by a forward projection on an image of the object.

In some embodiments, the imaging device 110 may be a non-invasive biomedical medical imaging device for disease diagnostic or research purposes. The imaging device 110 may include a single modality scanner and/or a multi-modality scanner. The single modality scanner may include, for example, an ultrasound scanner, an X-ray scanner, an computed tomography (CT) scanner, a magnetic resonance imaging (MRI) scanner, an ultrasonography scanner, a positron emission tomography (PET) scanner, an optical coherence tomography (OCT) scanner, an ultrasound (US) scanner, an intravascular ultrasound (IVUS) scanner, a near-infrared spectroscopy (NIRS) scanner, a far-infrared (FIR) scanner, a digital radiography (DR) device, or the like, or any combination thereof. The multi-modality scanner may include, for example, an X-ray imaging-magnetic resonance imaging (X-ray-MRI) scanner, a positron emission tomography-X-ray imaging (PET-X-ray) scanner, a single-photon emission computed tomography-magnetic resonance imaging (SPECT-MRI) scanner, a positron emission tomography-computed tomography (PET-CT) scanner, a digital subtraction angiography-magnetic resonance imaging (DSA-MRI) scanner, etc. It should be noted that the scanner described above is merely provided for illustration purposes, and not intended to limit the scope of the present disclosure. The term "imaging modality" or "modality" as used herein broadly refers to an imaging method or technology that gathers, generates, processes, and/or analyzes imaging information of an object.

For illustration purposes, the present disclosure mainly describes systems and methods relating to an X-ray imaging system. It should be noted that the X-ray imaging system described below is merely provided as an example, and not intended to limit the scope of the present disclosure. The systems and methods disclosed herein may be applied to any other imaging systems.

In some embodiments, the imaging device 110 may include a gantry 111, a detector 112, a detection region 113, a scanning table 114, and a radiation source 115. The gantry 111 may support the detector 112 and the radiation source 115. The object may be placed on the scanning table 114 and moved into the detection region 113 to be scanned. In some embodiments, the scanning table 114 may be configured to rotate and/or translate along different directions to move the object to a desired position. The radiation source 115 may emit radioactive rays to the object. The radioactive rays may include a particle ray, a photon ray, or the like, or a combination thereof. In some embodiments, the radioactive rays may include a plurality of radiation particles (e.g., neutrons, protons, electrons, p-mesons, heavy ions), a plurality of radiation photons (e.g., X-ray, γ-ray, ultraviolet, laser), or the like, or a combination thereof. The detector 112 may detect radiation and/or a radiation event (e.g., gamma photons) emitted from the detection region 113. In some embodiments, the detector 112 may include a plurality of detector units. The detector units may include a scintillation detector (e.g., a cesium iodide detector) or a gas detector. The detector unit may be a single-row detector or a multi-rows detector.

In some embodiments, the imaging device 110 may be or include an X-ray imaging device, for example, a computed tomography (CT) scanner, a digital radiography (DR) scanner (e.g., a mobile digital radiography), a digital subtraction angiography (DSA) scanner, a dynamic spatial reconstruction (DSR) scanner, an X-ray microscopy scanner, a multi-modality scanner, etc. For example, the X-ray imaging device may include a supporting device, an X-ray source, and a detector. The supporting device may be configured to support the X-ray source and/or the detector. The X-ray source may be configured to emit X-rays toward the object to be scanned. The detector may be configured to detect X-rays passing through the object. In some embodiments, the X-ray imaging device may be, for example, a C-shape X-ray imaging device, an upright X-ray imaging device, a suspended X-ray imaging device, or the like.

The processing device 120 may process data and/or information obtained from the imaging device 110, the storage device 130, and/or the terminal(s) 140. For example, the processing device 120 may implement an image acquisition operation on an object. As another example, the processing device 120 may implement an image processing operation on the object. More descriptions regarding the image acquisition operation and the image processing operation may be found elsewhere in the present disclosure. See, e.g., FIG. 10 and relevant descriptions thereof.

In some embodiments, the processing device 120 may be a single server or a server group. The server group may be centralized or distributed. In some embodiments, the processing device 120 may be local to or remote from the imaging system 100. For example, the processing device 120 may access information and/or data from the imaging device 110, the storage device 130, and/or the terminal(s) 140 via the network 150. As another example, the processing device 120 may be directly connected to the imaging device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

In some embodiments, the processing device 120 may include one or more processors (e.g., single-core processor(s) or multi-core processor(s)). Merely by way of example, the processing device 120 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 130 may store data, instructions, and/or any other information. In some embodiments, the storage device 130 may store data obtained from the processing device 120, the terminal(s) 140, and/or the imaging device 110. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components of the imaging system 100 (e.g., the processing device 120, the terminal(s) 140). One or more components of the imaging system 100 may access the data or instructions stored in the storage device 130 via the network 150. In some embodiments, the storage device 130 may be part of the processing device 120.

The terminal(s) 140 may enable user interaction between a user and the imaging system 100. For example, the terminal(s) 140 may display a result report of the object. As another example, the terminal(s) 140 may display guidance information to guide positioning of the object. In some embodiments, the terminal(s) 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 140 may include an input device, an output device, etc. In some embodiments, the terminal(s) 140 may be part of the processing device 120.

The network 150 may include any suitable network that can facilitate the exchange of information and/or data for the imaging system 100. In some embodiments, one or more components of the imaging system 100 (e.g., the imaging device 110, the processing device 120, the storage device 130, the terminal(s) 140) may communicate information and/or data with one or more other components of the imaging system 100 via the network 150. For example, the processing device 120 may obtain medical image data from the imaging device 110 via the network 150. As another example, the processing device 120 may obtain user instruction(s) from the terminal(s) 140 via the network 150.

The network 150 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the imaging system 100 may be connected to the network 150 to exchange data and/or information.

It should be noted that the above description of the imaging system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the imaging system 100 may include one or more additional components. Additionally or alternatively, one or more components of the imaging system 100, such as the imaging device 110 described above may be omitted. As another example, two or more components of the imaging system 100 may be integrated into a single component. Merely by way of example, the processing device 120 (or a portion thereof) may be integrated into the imaging device 110. In some embodiments, the imaging system 100 may further include a treatment device, such as a radiotherapy device.

FIG. 2 is a schematic diagram illustrating exemplary hardware and/or software components of a computing device 200 according to some embodiments of the present disclosure. The computing device 200 may be used to implement any component of the imaging system 100 as described herein. For example, the processing device 120 and/or the terminal 140 may be implemented on the computing device 200, respectively, via its hardware, software program, firmware, or a combination thereof. Although only one such computing device is shown, for convenience, the computer functions relating to the imaging system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, subjects, components, data structures, procedures, modules, and functions, which perform particular functions described herein. For example, the processor 210 may process image data obtained from the imaging device 110, the terminal(s) 140, the storage device 130, and/or any other component of the imaging system 100. In some embodiments, the processor 210 may include one or more hardware processors, such as a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the imaging device 110, the terminal(s) 140, the storage device 130, and/or any other component of the imaging system 100. In some embodiments, the storage device 220 may include a mass storage device, a removable storage device, a volatile read-and-write memory, a read-only memory (ROM), or the like, or any combination thereof. In some embodiments, the storage device 220 may store one or more programs and/or instructions to perform exemplary methods described in the present disclosure. For example, the storage device 220 may store a program for the processing device 120 to execute to perform an image acquisition operation on an object. As another example, the storage device 220 may store a program for the processing device 120 to execute to perform an image processing operation on the object.

The I/O 230 may input and/or output signals, data, information, etc. In some embodiments, the I/O 230 may enable a user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye-tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 150) to facilitate data communications. The communication port 240 may establish connections between the processing device 120 and the imaging device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
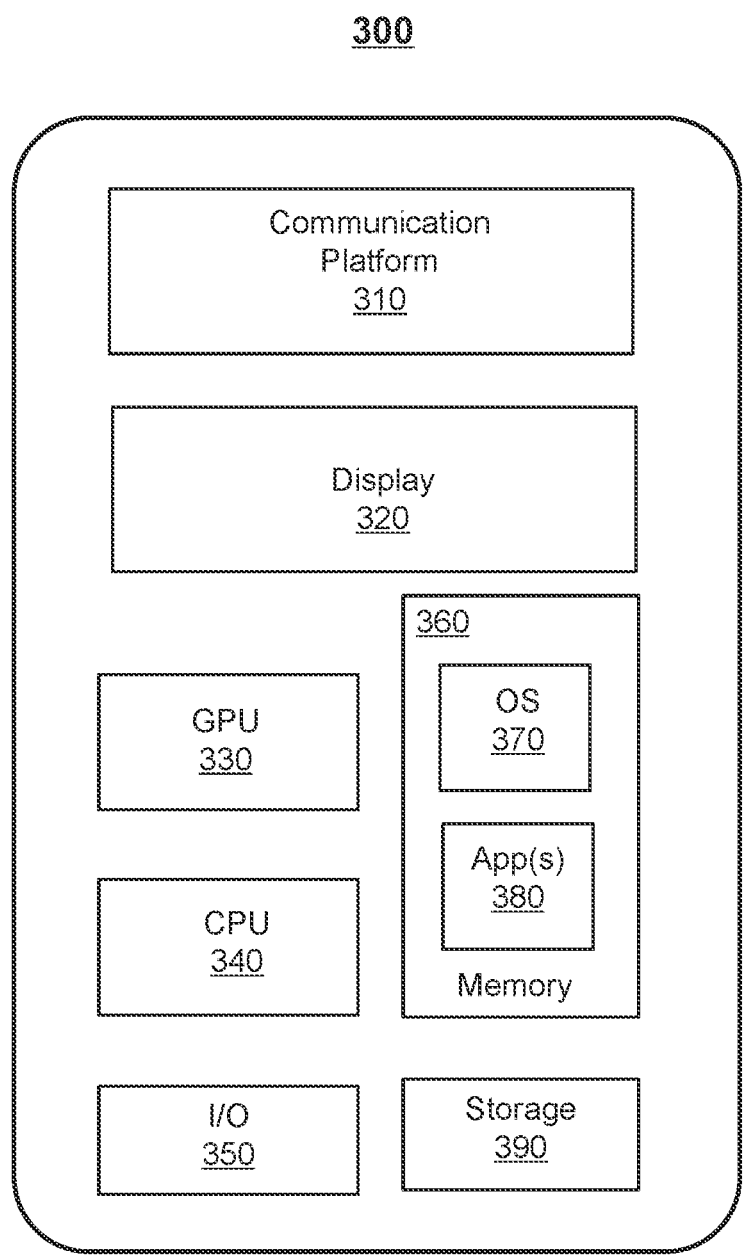
FIG. 3 is a schematic diagram illustrating hardware and/or software components of an exemplary mobile device according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 140 and/or the processing device 120) of the imaging system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the imaging system 100. User interactions with the information stream may be achieved via the I/O 350 and provided to the processing device 120 and/or other components of the imaging system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

A conventional medical imaging procedure often involves a lot of user intervention. For example, a user (e.g., a doctor, an operator, a technician, etc.) may need to manually operate a medical imaging device to image an object, which includes, for example, adjusting positions of at least two components (e.g., a detector and a tube) of the medical imaging device, guiding the object to maintain a specific posture, setting imaging parameters (e.g., exposure parameters), etc. Such a medical imaging process needs user intervention, causing inter-user variations, risks of human error, and/or low efficiency in the medical imaging procedure. Therefore, it is desirable to develop systems and methods for automated image acquisition during the medical imaging process, so as to improve efficiency and/or accuracy of imaging.

The present disclosure provides systems and methods for image acquisition. The systems and methods may automatically perform the image acquisition during the medical imaging process, and replace the manual operation of the user by automated positioning of an imaging device 110, automated guiding or controlling of the positioning of the object, automated imaging parameter setting, or other operations, thereby reducing or obviating user intervention in the imaging procedure, which in turn may save user time, reduce or avoid inter-user variation, risks of human error, and/or improve the efficiency and/or accuracy of the imaging procedure. In some embodiments, the system and method as disclosed herein may automatically or semi-automatically perform one or more of the following operations: obtaining identity information and inspection information of an object; determining, based on the identity information and the inspection information, at least target device positioning information of the imaging device 110; causing, based on the target device positioning information of the imaging device 110, the imaging device 110 to be positioned to perform the image acquisition; providing, based on the inspection information, guidance information, the guidance information being configured to guide positioning of the object; obtaining a target image from an imaging operation by the imaging device 110.

Figure 4:
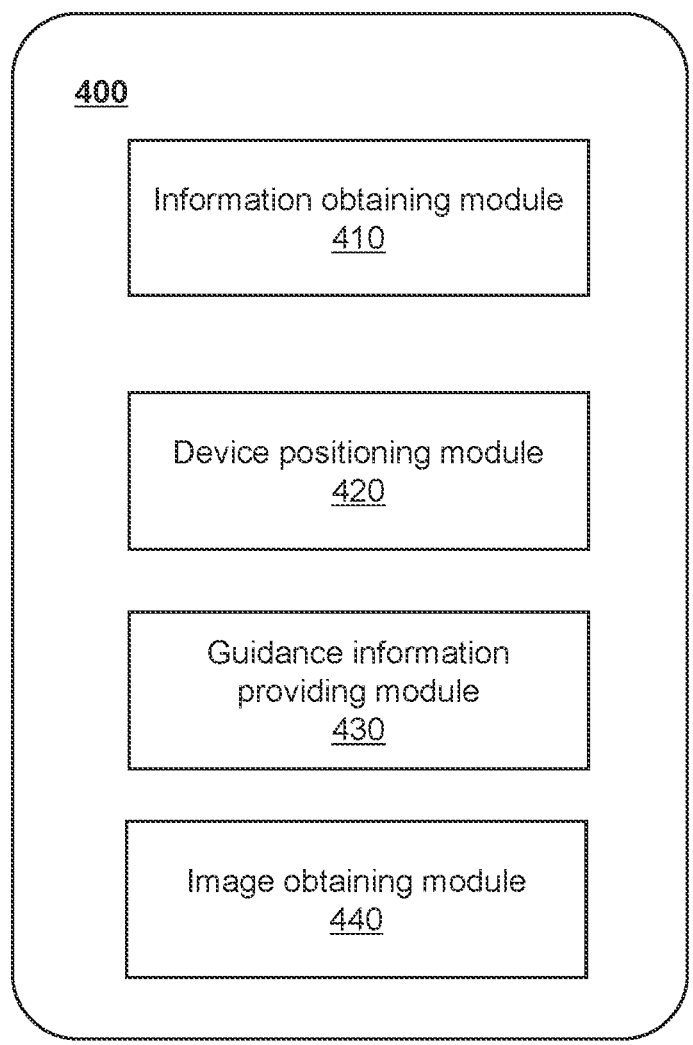
FIG. 4 is a block diagram illustrating an exemplary imaging system according to some embodiments of the present disclosure.

FIG. 4 is a block diagram illustrating an exemplary configuration 400 of the processing device 120 according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 4, the processing device 120 may include an information obtaining module 410, a device positioning module 420, a guidance information providing module 430, and an image obtaining module 440. Each of the modules described above may be a hardware circuit that is designed to perform certain actions, e.g., according to a set of instructions stored in one or more storage media, and/or any combination of the hardware circuit and the one or more storage media.

The information obtaining module 410 may be configured to obtain imaging information of an object. The imaging information may include identity information and inspection information. In some embodiments, the identity information may include personal information that may be used to verify the identity of the object. In some embodiments, the inspection information of the object may include information relating to the inspection to be performed on the object. In some embodiments, the information obtaining module 410 may obtain the identity information and the inspection information of the object from information input via the terminal device 140. In some embodiments, the information obtaining module 410 may also automatically obtain the physical characteristic information of the object according to a detection result of a detection device. In some embodiments, the information obtaining module 410 may obtain the inspection information and physical characteristic information corresponding to the personal information from the storage device 130 according to the personal information input through the terminal device 140. In some embodiments, the information obtaining module 410 may also determine the identity of the object through the personal information of the object acquired by an identity information acquisition device, and obtain the corresponding inspection information and physical characteristic information from the storage device 130 according to the personal information of the object.

The device positioning module 420 may be configured to determine, based on the identity information and the inspection information, the target device positioning information of the imaging device 110. In some embodiments, the imaging device 110 may be used to image the object or a portion of the object. As used herein, the target device positioning information of the imaging device 110 refers to the positioning information when the imaging device 110 starts an imaging operation or the positioning information when the imaging device 110 is ready for the imaging operation. In some embodiments, the device positioning module 420 may determine the target device positioning information of the imaging device 110 based on the physical characteristic information (e.g., the height, the weight, etc.) of the object. In some embodiments, the target device positioning information of the imaging device 110 may include positioning information of the detector and/or the radiation source. In some embodiments, the device positioning module 420 may determine the positions of the detector and the radiation source of the imaging device 110 based on the height of the object, the region of interest of the object to be imaged as specified in the inspection information, etc.

The device positioning module 420 may also be configured to cause, based on the target device positioning information of the imaging device, the imaging device 110 to be positioned to perform the image acquisition. In some embodiments, the device positioning module 420 may cause the one or more components (e.g., the radiation source, the detector, the patient support (e.g., a platform on which a patient may stand when the patient is being imaged, a bed on which a patient may lie when the patient is being imaged)), a gantry, etc.) of the imaging device 110 to move based on the target device positioning information of the imaging device 110. In some embodiments, the device positioning module 420 may cause the imaging device 110 to move based on current device positioning information and the target device positioning information of the imaging device 110.

In some embodiments, the device positioning module 420 may be further configured to generate a control instruction according to the target device positioning information of the imaging device 110, and cause the imaging device 110 to move based on the control instruction. In some embodiments, the device positioning module 420 may determine a motion path of the imaging device 110, or a portion thereof, based on the target device positioning information of the imaging device 110, and cause the imaging device 110, or a portion thereof, to move based on the motion path. In some embodiments, the control instruction may include the motion path of the imaging device 110, or a portion thereof. In some embodiments, the control instruction may include a coarse adjustment instruction and a fine adjustment instruction. In some embodiments, the device positioning module 420 may directly cause the imaging device 110 to be moved based on the control instruction. Alternatively, the device positioning module 420 may transmit the control instruction to the imaging device 110, and one or more components of the imaging device 110 may execute the control instruction.

The imaging device 110 may be adjusted from the current position to the target position according to the control instruction.

The guidance information module 430 may be configured to provide, based on the inspection information, guidance information. The guidance information may be configured to guide positioning of the object. In some embodiments, based on the target device positioning information of the imaging device 110 and the inspection information, the guidance information module 430 may determine target patient positioning information of the object, and determine the guidance information according to the target patient positioning information. As used herein, the target patient positioning information refers to the positioning information of a target position of the object. In some embodiments, the guidance information module 430 may determine the guidance information based on a current patient positioning information of the object and the target patient positioning information of the object. In some embodiments, the guidance information module 430 may obtain the current patient positioning information of the object. In some embodiments, the guidance information module 430 may compare the current patient positioning information of the object with the target patient positioning information of the object, and determine the guidance information according to a comparison result between the current patient positioning information of the object and the target patient positioning information of the object. The comparison result between the current patient positioning information of the object and the target patient positioning information of the object may include the difference between the current patient positioning information of the object and the target patient positioning information of the object.

In some embodiments, the guidance information module 430 may determine the guidance information based on a positioning angle difference between the current patient positioning information and the target patient positioning information of the object and a distance difference between the object (e.g., the region of interest of the object) and the one or more components of the imaging device 110. The guidance information may guide the object to rotate a certain angle in a certain direction and/or move a certain distance in a certain moving direction, thereby causing the object to move to the target position corresponding to the target patient positioning information of the object. In some embodiments, the guidance information module 430 may generate a positioning reference image according to the target patient positioning information of the object, and then determine the guidance information according to the current patient positioning information of the object and the positioning reference image. The guidance information module 430 may compare the current patient positioning information of the object with the positioning reference image, and determine the guidance information according to a comparison result.

In some embodiments, the guidance information module 430 may also put the current patient positioning information and the positioning reference image in a same coordinate system for comparison and/or simultaneous display. In some embodiments, if the current patient positioning information is presented in the form of an image, the current positioning image and the positioning reference image may be fused or superimposed to visually illustrate the difference between a current posture of the object and the posture in the fused or superimposed image. In some embodiments, if the current patient positioning information includes the non-image information, the non-image information may be processed first.

The image obtaining module 440 may be configured to obtain a target image from an imaging operation using the imaging device 110. The imaging operation may include an exposure operation. In some embodiments, the imaging operation may be understood as an operation for obtaining an imaging image according to imaging parameters. After the imaging device 110 and the object are both positioned, the operation may be performed, and the image obtaining module 440 may obtain the target image generated by the imaging operation. In some embodiments, when the imaging device 110 and the object are both positioned, the image obtaining module 440 may transmit an imaging instruction to the imaging device 110 to cause the imaging device 110 to automatically perform an imaging operation according to target imaging information.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the device positioning module 420 and the guidance information module 430 may be integrated into a single module. As another example, some other components/modules may be added into the processing device 120.

Figure 5:
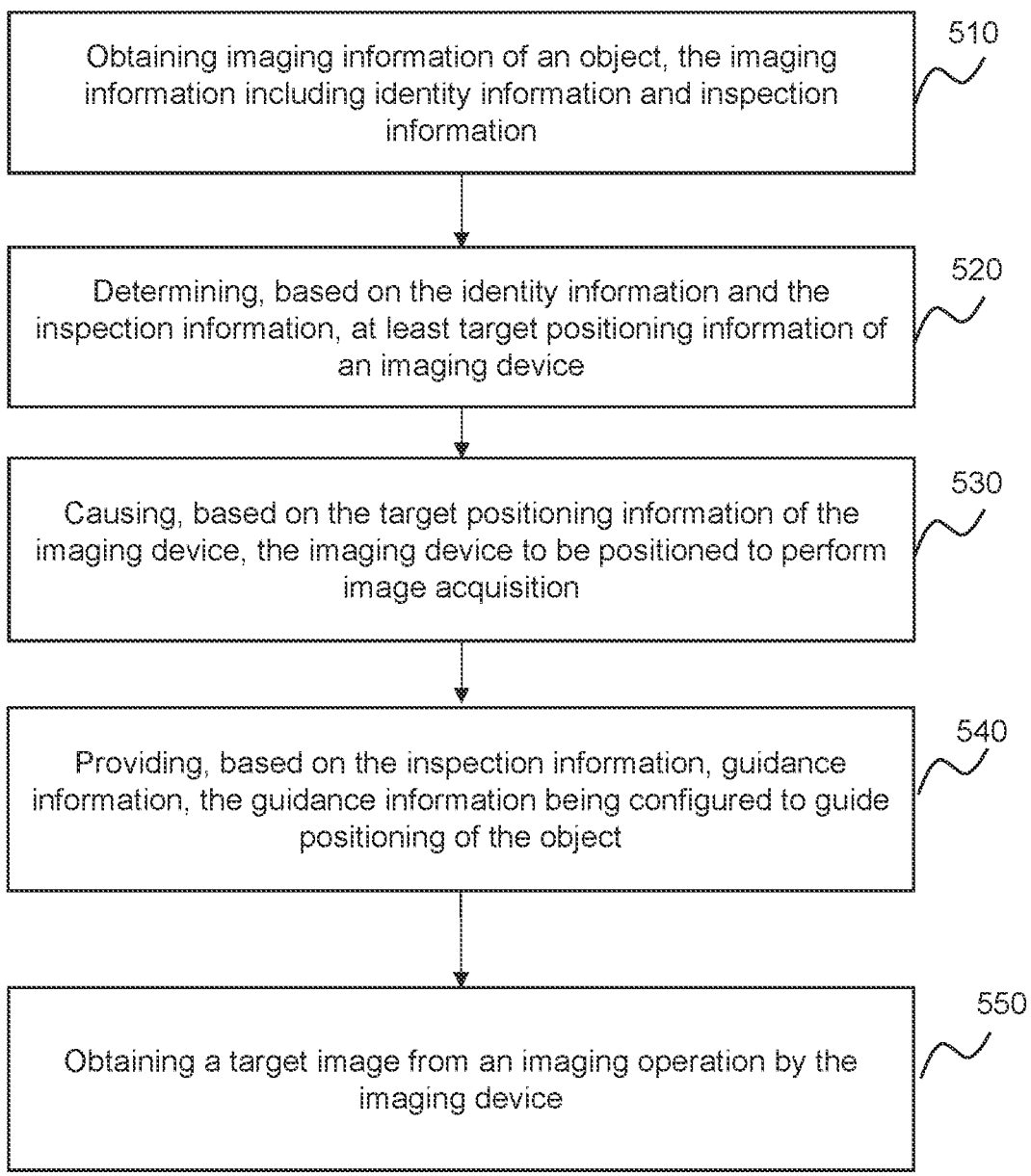
FIG. 5 is a flowchart illustrating an exemplary process for image acquisition according to some embodiments of the present disclosure.

FIG. 5 is a flowchart illustrating an exemplary process for image acquisition according to some embodiments of the present disclosure. In some embodiments, process 500 may be implemented as a set of instructions (e.g., an application) stored in the storage device 130, storage device 220, or storage 390. The processing device 120, the processor 210, and/or the CPU 340 may execute the set of instructions, and when executing the instructions, the processing device 120, the processor 210, and/or the CPU 340 may be configured to perform the process 500. The operations of the illustrated process presented below are intended to be illustrative. In some embodiments, the process 500 may be accomplished with one or more additional operations not described and/or without one or more of the operations discussed. Additionally, the order of the operations of the process 500 illustrated in FIG. 5 and described below is not intended to be limiting.

In 510, the processing device 120 (e.g., the information obtaining module 410) may obtain imaging information of an object. The imaging information may include identity information and inspection information.

In some embodiments, the object may include a biological object and/or a non-biological object. For example, the object may be a patient on whom image acquisition is to be performed by the imaging system 100. In some embodiments, the identity information of the object may include physical characteristic information that reflects one or more physical characteristics of the object. For instance, the identity information of the object may include a height, the weight, the shape, or the like, or a combination thereof, of the object. In some embodiments, the physical characteristic of the object may be used to determine target device positioning information of the imaging device 110. More descriptions regarding determining the target device positioning information of the imaging device 110 may be found in operation 520.

In some embodiments, the identity information may include personal information that may be used to verify the identity of the object. The personal information may be used to verify that an imaging procedure is performed on a right object. For instance, the identity information of the object may include a government-issued identity number, name, gender, age, birthday, a medical/patient record number, a reservation number or confirmation number of a medical procedure (e.g., an imaging procedure), biometric information, or the like, or any combination thereof, of the object. Exemplary biometric information of the object may include information of facial recognition, voiceprint, fingerprint, etc., of the object.

In some embodiments, the inspection information of the object may include information relating to the inspection to be performed on the object. In some embodiments, the inspection information may include information identifying or otherwise relating to at least a region of interest of the object (e.g., a chest, a head, etc.). In some embodiments, the inspection information may further include the imaging device 110 (e.g., an X-ray imaging device, a PET device, an MRI device, etc.) used for the inspection.

In some embodiments, the processing device 120 (e.g., the information obtaining module 410) may obtain the identity information and the inspection information of the object from information input via the terminal device 140. In some embodiments, the identity information of the object (e.g., the physical characteristic information or the personal information) may be input into the terminal device 140 by the object. Alternatively, the identity information of the object may be input into the terminal device 140 by a user (e.g., a doctor, a technician, etc.). For instance, the inspection information of the object may be input into the terminal device 140 by the user based on a diagnosis result (e.g., a diagnosis report held by the object) and/or information provided by the object. In some embodiments, the identity information and the inspection information input into the terminal device 140 may be sent to the processing device 120 for further processing. In some embodiments, the object or the user may input the identity information and the inspection information to the terminal device 140 through a keyboard, a touch screen, voice, or the like.

In some embodiments, the processing device 120 (e.g., the information obtaining module 410) may also automatically obtain the physical characteristic information of the object according to a detection result of a detection device. For example, after the object stands at a detection position, the detection device may automatically detect at least a portion of the physical characteristic information such as the height, the body thickness, or the weight of the object, and transmit the detection result to the terminal device 140 or the processing device 120. In some embodiments, the detection device may include a distance measurement sensor or a mass or pressure sensor. As used herein, the distance measurement sensor may be used to detect the height or body thickness of the object. The mass or pressure sensor may be used to detect the weight of the object.

In some embodiments, the personal information, physical characteristic information, and inspection information of the object may be pre-stored in the storage device 130. In some embodiments, in the pre-stored information, the correspondence between different inspection information and different objects may be denoted using the identity information. For example, inspection information of an object whose name is John and identification number is 123456 may show that a chest radiograph is scheduled to be performed on the object. In some embodiments, the processing device 120 may obtain the inspection information and physical characteristic information of the object from the storage device 130 according to the identity information of the object.

In some embodiments, the processing device 120 may obtain the inspection information and physical characteristic information corresponding to the personal information from the storage device 130 according to the personal information input through the terminal device 140. For example, the technician may also first ask the object of his name or inspection number and enter the name or inspection number into the terminal device 140. The terminal device 140 may automatically obtain the inspection information and physical characteristic information corresponding to the name or inspection number from the storage device 130, and transmit the acquired inspection information and physical characteristic information to the processing device 120.

In some embodiments, the processing device 120 may also determine the identity of the object through the personal information of the object acquired by an identity information acquisition device, and obtain the corresponding inspection information and physical characteristic information from the storage device 130 according to the personal information of the object. In some embodiments, the identity information acquisition device may include an image acquisition device, a fingerprint acquisition device, a voice recognition device, or the like. The image acquisition device may be used to acquire an image of the object, or a portion thereof (e.g., a facial image). The fingerprint acquisition device may be used to acquire a fingerprint of the object. In some embodiments, an identity information database may be established based on the identity information of a plurality of objects and pre-stored in the storage device 130. In some embodiments, the identity information database may include a facial image database, a fingerprint information database, or the like. The processing device 120 may identify the object based on acquired identity information and the identity information database. For example, when the object enters the inspection room, the image acquisition device (or the fingerprint acquisition device) may acquire a facial image (or fingerprint information) of the object, and the processing device 120 may search the facial image database (or the fingerprint information in the fingerprint information database) for a facial image (or fingerprint) that matches the acquired facial image (or the acquired fingerprint), in order to determine the identity of the object. Subsequently, the processing device 120 may retrieve the physical characteristic information and inspection information corresponding to the identity from the storage device 130.

In some embodiments, since the physical characteristic information (e.g., the height and the weight) of the object may change over time, in order to obtain accurate physical characteristic information, the physical characteristic information (e.g., the height, the weight, the physical characteristic, etc.) of the object may be obtained on site as part of the process of the image acquisition (e.g., the preparation or setup portion of the image acquisition process). In some embodiments, the processing device 120 may obtain the physical characteristic information from data input on the terminal device 140. The processing device 120 may also obtain the physical characteristic information from the detection result of the detection device (e.g., the distance measurement sensor or the mass or pressure sensor). In some embodiments, the processing device 120 may also obtain a full-body image of the object using the image acquisition device, and then determine the physical characteristic information of the object through an image processing algorithm.

In some embodiments, whether the physical characteristic information of the object needs to be acquired on site may also be determined according to a validity period. For instance, the physical characteristic information may be pre-stored in the storage device 130, and a validity period for the physical characteristic information may be set. When the object enters the inspection room for the inspection, the processing device 120 may identify the time of the latest update of the physical characteristic information of the object and determine whether the validity period for the information has elapsed. If the validity period for the information has elapsed, the processing device 120 may provide a prompt indicating that the physical characteristic information of the object needs to be re-measured on site, and the corresponding physical characteristic information in the storage device 130 needs to be updated based on the measurement result. If the physical characteristic information is within its validity period, there may be no need to re-measure on-site, and the physical characteristic information in the storage device 130 may be used as the physical characteristic information for this inspection. In some embodiments, the validity period may be in the range from 1 week and a year. In some embodiments, the validity period may be set based on conditions of the object including, e.g., age, health condition, inspection to be performed (e.g., whether the inspection to be performed is sensitive to the physical characteristic information), or the like, or a combination thereof. For instance, if the object is an infant less than a year old, the validity period of the physical characteristic information may be short, e.g., 3 days, 1 week, etc. As another example, if the object is an adult generally in good health, the validity period of the physical characteristic information may be long, e.g., 3 months, 6 months, 8 months, 12 months.

In 520, the processing device 120 (e.g., the device positioning module 420) may determine, based on the identity information and the inspection information, the target device positioning information of the imaging device 110.

In some embodiments, the imaging device 110 may be used to image the object or a portion of the object. In some embodiments, the imaging device may be an X-ray imaging device (e.g., a suspended X-ray imaging device, a C-arm X-ray imaging device), a digital radiography (DR) device (e.g., a mobile digital X-ray imaging device), a CT device, a PET device, an MRI device, etc. More descriptions regarding the imaging device may be found in FIG. 1 and the descriptions thereof.

Unless otherwise stated, the following descriptions are provided with reference to the imaging device 110 including a DR device for the purposes of illustration, and not intended to be limiting.

As used herein, the target device positioning information of the imaging device 110 refers to the positioning information when the imaging device 110 starts an imaging operation or the positioning information when the imaging device 110 is ready for the imaging operation. In some embodiments, the positioning information may include a spatial position of at least one of various components (e.g., a radioactive source (e.g., a tube), a detector, an inspection table, etc.) in the imaging device 110.

In some embodiments, the processing device 120 may determine the target device positioning information of the imaging device 110 based on the physical characteristic information (e.g., the height, the weight, etc.) of the object.

In some embodiments, the target device positioning information of the imaging device 110 may include positioning information of the detector and/or the radiation source. In some embodiments, the processing device 120 may determine the positions of the detector and the radiation source of the imaging device 110 based on the height of the object, the region of interest of the object to be imaged as specified in the inspection information, etc. For example, if the inspection information specifies that a chest radiograph is to be performed on the object, the position of the detector may need to correspond to the position of the chest of the object when the object is positioned for imaging. The higher the height of the object, the higher the position of the detector may need to be. That is, the height of different objects may correspond to different positions of the detector. After the position of the detector is determined, the position of the tube may need to be set corresponding to the position of the detector. For example, if the inspection information specifies that a left knee of the object is to be imaged from two angles with respect to a specific orientation of the left knee, a length of the left leg of the object and/or the position of the left knee of the object when positioned for imaging may be estimated based on the height of the object, and the positions of the detector and the tube for imaging of the left knee from the two angles may be determined according to the estimated length of the leg, the estimated position of the left knee, and the orientation of the left leg or the left knee.

In some embodiments, if the object is overweight, in order to obtain a relatively clear image, a distance between the tube and the detector may be reduced than if the object is relatively skinny. That is, a source image distance (SID) may be reduced if the object is overweight than if the object is skinny. In some embodiments, the physical characteristic of the object may be reflected by the body thickness. For instance, the larger the body thickness of the object is, the more overweight the object may be. In some embodiments, the physical characteristic of the object may be represented by weight. In some embodiments, the physical characteristic of the object may be reflected by a combination of the weight and the height, e.g., the body mass index.

In 530, the processing device 120 (e.g., the device positioning module 420) may cause, based on the target device positioning information of the imaging device, the imaging device 110 to be positioned to perform the image acquisition.

In some embodiments, the processing device 120 may cause the one or more components (e.g., the radiation source, the detector, the patient support (e.g., a platform on which a patient may stand when the patient is being imaged, a bed on which a patient may lie when the patient is being imaged)), a gantry, etc.) of the imaging device 110 to move based on the target device positioning information of the imaging device 110. In some embodiments, the processing device 120 may cause the imaging device 110 to move based on current device positioning information and the target device positioning information of the imaging device 110. As used herein, current device positioning information refers to the positioning information of a current position of the imaging device 110. As used herein, target positioning information refers to the positioning information of a target position of the imaging device 110. In some embodiments, the processing device 120 may also directly cause the imaging device 110 to move to a target position based on the target device positioning information.

In some embodiments, the processing device 120 (e.g., the device positioning module 420) may generate a control instruction according to the target device positioning information of the imaging device 110, and cause the imaging device 110 to move based on the control instruction.

In some embodiments, the processing device 120 (e.g., the device positioning module 420) may determine a motion path of the imaging device 110, or a portion thereof, based on the target device positioning information of the imaging device 110, and cause the imaging device 110, or a portion thereof, to move based on the motion path. In some embodiments, the control instruction may include the motion path of the imaging device 110, or a portion thereof. For instance, the processing device 120 (e.g., the device positioning module 420) may also determine the motion path based on the target device positioning information of the imaging device 110 and the current position of the imaging device 110, and cause the imaging device 110 to move based on the motion path. As another example, if multiple components of the imaging device 110 need to move, the processing device 120 may determine a control instruction for each of the multiple components of the imaging device 110, and cause each of the components to move according to the corresponding control instruction so that the imaging device 110 is positioned at the target position. For convenience, the following descriptions are provided with respect to one component of the imaging device 110 to be moved according to a control instruction, unless otherwise stated. It is understood that this is for illustration purposes only and not intended to be limiting.

In some embodiments, the control instruction may include a coarse adjustment instruction and a fine adjustment instruction. Therefore, the processing device 120 may cause the position of the imaging device 110 to be adjusted to the target position according to the coarse adjustment instruction and/or the fine adjustment instruction. As used herein, the coarse adjustment instruction refers to a control instruction with a relatively large motion range, for example, the motion path of the detector or the tube of the imaging device 110. As used herein, the fine adjustment instruction refers to a control instruction with a relatively small motion range, for example, a swing of the detector or the tube within a certain angle range. In some embodiments, the control instruction may include an instruction for adjusting a height of the patient support, a scanning angle, the SID, or the like, or a combination thereof.

In some embodiments, the processing device 120 (e.g., the device positioning module 420) may directly cause the imaging device 110 to be moved based on the control instruction. Alternatively, the processing device 120 may transmit the control instruction to the imaging device 110, and one or more components of the imaging device 110 may execute the control instruction. The imaging device 110 may be adjusted from the current position to the target position according to the control instruction.

In 540, the processing device 120 (e.g., the guidance information module 430) may provide, based on the inspection information, guidance information. The guidance information may be configured to guide positioning of the object.

In some embodiments, the positioning of the object may include adjusting a posture (e.g., standing, lying on a side, lying on the back, lying on the stomach, etc.) of the object to get ready to be imaged using the imaging device 110. In some embodiments, the positioning of the object may include at least one of an active positioning of the object or a passive positioning of the object. As used herein, the active positioning of the object means that the object performs a positioning operation himself by adjusting his posture and/or position according to the guidance information. As used herein, the passive positioning of the object means that the posture and/or position of the object is adjusted by the movement of a positioning device (e.g., the patient support) according to the guidance information. During an active positioning, the guidance information may be presented to the object. For example, the guidance information may be display on a screen. During a passive positioning, the guidance information may be directly output to the positioning device or a device that controls the movement of the positioning device, and the positioning device may take the object to the corresponding position according to the guidance information.

In some embodiments, based on the target device positioning information of the imaging device 110 and the inspection information, the processing device 120 may determine target patient positioning information of the object, and determine the guidance information according to the target patient positioning information. As used herein, the target patient positioning information refers to the positioning information of a target position of the object. For instance, the processing device 120 may determine the target patient positioning information of the object based on the region of interest of the object as specified in the inspection information. The target patient positioning information of the object may be understood as the positioning information of the object when the imaging device 110 starts the imaging operation or when the imaging device 110 is ready for the imaging operation. The target patient positioning information may include, for example, the target posture or the target position of the object. When the imaging operation starts or when the imaging operation is ready, the target patient positioning information of the object may need to correspond to the target device positioning information of the imaging device 110 so that the position of the detector or the tube may correspond to the region of interest of the object to improve accuracy of the inspection or imaging.

Merely by way of example, to image the chest of the object using the imaging device 110, the target patient positioning information of the object may include that the chest of the object needs to be positioned close to the detector of the imaging device 110, and the guidance information may include guiding the object to adjust the posture so that the chest of the object is facing the detector of the imaging device 110. As used herein, a region of interest of an object being close to the detector of an imaging device indicates that an average distance between the region of interest and the detector (or between the region of interest and a field of view (FOV) or a portion thereof (e.g., a center region of the FOV, an isocenter plane) of the imaging device 110) is less than a threshold practical and/or desirable with respect to imaging using the imaging device 110.

In some embodiments, the guidance information for an active positioning may include an instruction indicating a target posture of the object relative to the detector or other components of the imaging device 110, a target position of the object, or the like, or a combination thereof. The object himself may adjust to the target posture and/or target position. In some embodiments, the guidance information for a passive positioning may include motion parameters (e.g., a motion distance, a motion direction, etc.) according to which a positioning device is to move so as to position the object.

In some embodiments, the processing device 120 may determine the guidance information based on a current patient positioning information of the object and the target patient positioning information of the object. As used in here, the current patient positioning information refers to the positioning information of a current position of the object. For instance, the processing device 120 may determine the guidance information according to a difference between the current patient positioning information and the target patient positioning information.

In some embodiments, the processing device 120 may obtain the current patient positioning information of the object. In some embodiments, the processing device 120 may compare the current patient positioning information of the object with the target patient positioning information of the object, and determine the guidance information according to a comparison result between the current patient positioning information of the object and the target patient positioning information of the object. The comparison result between the current patient positioning information of the object and the target patient positioning information of the object may include the difference between the current patient positioning information of the object and the target patient positioning information of the object.

The target patient positioning information of the object refers to the position information of the object when the positioning starts, and the positioning angle and the positioning direction of the object when the positioning starts. In some embodiments, the current patient positioning information of the object may also include a distance between the object or the region of interest of the object and the one or more components of the imaging device 110. In some embodiments, the one or more components refer to one or more mobile components on the imaging device. For instance, a radiation source, a detector, and a gantry used to support the radiation source and/or the detector. In some embodiments, the positioning angle and positioning direction of the object may be an angle and a direction of the object (e.g., the region of interest of the object) relative to the imaging device 110 or the one or more components (e.g., the radiation source, the detector, the gantry) of the imaging device 110. In some embodiments, the current patient positioning information of the object may be obtained by a sensor or a camera installed in the inspection room or by the imaging device 110. The sensor may include an infrared sensor, a laser sensor, etc.

In some embodiments, the processing device 120 may determine the guidance information based on a positioning angle difference between the current patient positioning information and the target patient positioning information of the object and a distance difference between the object (e.g., the region of interest of the object) and the one or more components of the imaging device 110. The guidance information may guide the object to rotate a certain angle in a certain direction and/or move a certain distance in a certain moving direction, thereby causing the object to move to the target position corresponding to the target patient positioning information of the object.

Merely by way of example, the current patient positioning information of the object may include a first positioning angle, a first distance, a first positioning direction, or the like, or any combination thereof; the target patient positioning information of the object may include a second positioning angle, a second distance, and a second positioning direction, or the like, or any combination thereof. The imaging system 100 may obtain a comparison result between the current patient positioning information of the object and target patient positioning information of the object by comparing the first positioning angle with the second positioning angle, comparing the first distance with the second distance, and comparing the first positioning direction with the second positioning direction, respectively. The comparison result may include a difference between the first angle and the second angle, a difference between the first distance and the second distance, a difference between the first direction and the second direction, or the like, or any combination thereof. Further, the guidance information may include information guiding the object to be positioned from the first angle to the second angle, from the first distance to the second distance, and from the first direction to the second direction.

In some embodiments, the processing device 120 may generate a positioning reference image according to the target patient positioning information of the object, and then determine the guidance information according to the current patient positioning information of the object and the positioning reference image. In some embodiments, the positioning reference image may reflect the target position or posture of the object. The processing device 120 may compare the current patient positioning information of the object with the positioning reference image, and determine the guidance information according to a comparison result. In some embodiments, the positioning reference image may be one or more images showing that the posture or position of the object should be maintained during the imaging operation. For example, the positioning reference image may be a schematic diagram of the object holding the detector on his chest. In some embodiments, the current patient positioning information of the object may be presented in a current positioning image of the object, and other non-image information that reflects the current posture or position of the object (e.g., the positioning angle and the positioning direction). For instance, the current positioning image may be obtained by a camera (e.g., an infrared camera or an optical camera) installed in the inspection room. Exemplary non-image information may include coordinate data relating to a position of the object.

In some embodiments, the comparison result between the current patient positioning information of the object and the positioning reference image may include a matching degree between the current patient positioning information of the object and the positioning reference image. In some embodiments, the guide information may include the positioning reference image and the matching degree between the current patient positioning information of the object and the positioning reference image. As used herein, the matching degree between the current patient positioning information of the object and the positioning reference image reflects the difference between the current patient positioning information of the object and the target patient positioning information of the object. The processing device 120 may determine, based on the matching degree, whether to continue to cause the positioning of the object to be adjusted. For example, if the guidance information includes that the matching degree between the current position information and the position reference image is 50%, the processing device 120 may determine that the positioning of the object needs to be further adjusted. In some embodiments, if the matching degree between the current patient positioning information and the positioning reference image exceeds a threshold, e.g., 90%, 95%, the processing device 120 may determine that the target positioning of the object is achieved. In some embodiments, the processing device 120 may generate a prompt message informing the object the completion of the positioning operation.

In some embodiments, the processing device 120 may also put the current patient positioning information and the positioning reference image in a same coordinate system for comparison and/or simultaneous display. In some embodiments, if the current patient positioning information is presented in the form of an image, the current positioning image and the positioning reference image may be fused or superimposed to visually illustrate the difference between a current posture of the object and the posture in the fused or superimposed image. In some embodiments, if the current patient positioning information includes the non-image information, the non-image information may be processed first. For example, if the current patient positioning information includes coordinate data relating to a position of the object, the processing device 120 may convert the coordinate data to the form of an image that displays the posture of the object corresponding to the current patient positioning information.

In some embodiments, the positioning reference image may be generated based on a basic human body image and the target patient positioning information of the object. As used herein, a basic human body image refers to a human body image including a representation of a portion of the human body that encompasses more than merely the object. For example, if the object is an adult or a portion of the adult, the processing device 120 may generate the positioning reference image based on a basic human body image, in which the basic human body image may include a representation of a portion of the adult that encompasses and is larger than the object. In some embodiments, the positioning reference image may also be generated based on information of a physical characteristic of the object and the target patient positioning information of the object. As used herein, a physical characteristic of the object may be retrieved from pre-established personal information according to the identity information of the object. The physical characteristic may be described using one or more parameters including the height, the weight, the physical, etc. By adjusting the position and/or posture of the object to approach the target positioning in the positioning reference image, the current positioning image of the object may be consistent with the positioning reference image. Therefore, the accuracy of guiding the positioning of the object may be improved.

According to different scenarios of the active positioning and passive positioning, in some embodiments, the guidance information may be output to the object, so that the object may actively perform the positioning operation himself by adjusting his posture and/or position according to the guidance information. In some embodiments, the guidance information may also be output to the positioning device, and the posture and/or position of the object may be adjusted by the movement of a positioning device (e.g., the patient support) according to the guidance information. In some embodiments, the processing device 120 may also directly output the guidance information to the positioning device or the device that controls the movement of the positioning device, and the positioning device may take the object to the corresponding position according to the guidance information.

In some embodiments, the object may perform an active positioning operation based on an output result of the guidance information. As used herein, output modes of the guidance information may include a voice output, a display, etc., or a combination thereof. Correspondingly, guidance modes may include a voice guidance mode or a display guidance mode. In some embodiments, under the display guidance mode, the positioning reference image and/or the guidance information may be displayed on a display device. In some embodiments, the display device may include a monitor, a TV, a screen, etc. The guidance information may include keywords (e.g., standing, lying on the side, lying down, etc.), images (e.g., the positioning reference image of the object, the current positioning image of the object, etc.), videos, etc., displayed on the display device to guide the object to position. In some embodiments, the guidance information may be displayed and simultaneously broadcasted. For example, the imaging system 100 may guide the positioning of the object by a demonstration on the display device to facilitate the active positioning of the object.

Merely by way of example, the display guidance mode may be achieved by installing a camera and a visual positioning assistant (e.g., a display, a TV, etc.) in the inspection room. The processing device 120 may obtain the current positioning image of the object (e.g., a right hand) in real time from the camera, and compare in real time the obtained current positioning image of the object with the positioning reference image to obtain a comparison result between the (substantially) real-time current positioning image of the object and the positioning reference image. The guidance information for guiding the positioning of the object may be determined based on the comparison result. In addition, the visual positioning assistant may visualize information (e.g., the positioning reference image) and the current positioning images obtained by the camera in real time to guide the positioning adjustment of the object.

As another example, the display guidance mode may be implemented by installing a projection positioning assistant (e.g., a screen) in the inspection room. The image of the object (e.g., the right hand) may be obtained in real time using a camera, and the image of the object obtained in real time may be compared with the positioning reference image to obtain the comparison result between the (substantially) real-time current patient positioning information of the object and the positioning reference object. The guidance information for guiding the positioning of the object may be determined based on the comparison result. In addition, the projection positioning assistant may visualize the information on the screen to display a projection of the positioning reference image (or a correct positioning at the time of imaging) of the object. When the positioning of the object is successful, the processing device 120 may generate a prompt message informing the object the completion of the positioning operation. When the positioning of the object is failing, the processing device 120 may generate a prompt message informing the object to reposition.

Merely by way of example, when the object is lying on the inspection table for imaging the head, the processing device 120 may generate the positioning reference image according to the target positioning information of the object and project the positioning reference image onto the screen. If it is determined that the head in the current positioning image is to the left compared to its target positioning in the positioning reference image, the imaging system 100 may automatically generate guidance information to guide the adjustment of the head to the right until the head of the object in the current positioning image coincides with a target head position in the positioning reference image. In some embodiments, while the positioning of the object is being adjusted, the imaging system 100 may continue (e.g., at a time interval) to capture the current patient positioning information of the object, and determine the difference between the current patient positioning information of the object and the target patient positioning information (e.g., the positioning reference image). The object may continue to perform the positioning until the difference between the current patient positioning information of the object and the target patient positioning information is zero or less than a certain threshold.

In some embodiments, the voice guidance mode may be implemented by installing the camera and a voice assistant in the inspection room. For instance, the processing device 120 may obtain the current positioning image of the object (e.g., the right hand) in real time from the camera, and compare in real time the obtained current positioning image of the object with the positioning reference image to obtain a comparison result between a (substantially) real-time current positioning image of the object and the positioning reference image. The guidance information for guiding the positioning of the object may be determined based on the comparison result. The voice assistant may prompt the object to perform a next motion to complete the positioning using voice e.g., "move head to the left," "arms on both sides of the thigh," etc.) based on the information (e.g., the positioning reference image) and the current positioning image obtained by the camera in real time. In some embodiments, after the positioning of the object is successful, the processing device 120 may generate a prompt message informing the object the completion of the positioning by the voice assistant. When the positioning of the object is failing, the processing device 120 may generate a prompt message informing the object to reposition by the voice assistant.

In 550, the processing device 120 (e.g., the image obtaining module 440) may obtain a target image from an imaging operation using the imaging device 110.

In some embodiments, the imaging operation may include an exposure operation. The imaging operation may be understood as an operation for obtaining an imaging image according to imaging parameters. In some embodiments, after the imaging device 110 and the object are both positioned, the operation may be performed, and the processing device 120 may obtain the target image generated by the imaging operation. As used herein, the imaging operation of the imaging device 110 may be automatically performed by the imaging device 110 based on a control instruction from the processing device 120. Alternatively, the imaging operation may be completed by a user (e.g., a doctor, a technician) manually operating the imaging device 110.

In some embodiments, when the imaging device 110 and the object are both positioned, the processing device 120 may transmit an imaging instruction to the imaging device 110 to cause the imaging device 110 to automatically perform an imaging operation according to target imaging information. The target imaging information may include target exposure information. As used herein, the target exposure information of the imaging device 110 may be determined when the target patient positioning information of the imaging device 110 is determined in operation 520. In some embodiments, the target exposure information of the imaging device 110 may include information relating to the exposure operation of the imaging device 110 on the object. In some embodiments, the target exposure information of the imaging device 110 may include the speed of motion or rotation of one or more components (e.g., the patient support, the gantry, etc.) of the imaging device 110, an exposure duration of the imaging device 110 during the image acquisition, an exposure dose (e.g., the radiation dose), a light field size, a voltage value of the tube, a current value of the tube, a focal length of the tube, etc. For example, the processing device 120 may determine the exposure duration, the exposure dose, the light field size, etc., of the imaging device 110 based on the identity information (e.g., the height, the weight, or the body thickness) of the object and the inspection information (e.g., the region of interest).

Merely by way of example, after determining that the object completes the positioning, the processing device 120 may transmit the imaging instruction to the imaging device 110. When the imaging device 110 receives the imaging instruction, the imaging device 110 may perform the imaging operation on the object according to the target imaging information corresponding to the imaging instruction. The imaging system 100 may automatically perform the imaging operation to obtain the target image. It may be unnecessary for the user (e.g., the doctor or the technician) to manually adjust the target imaging information after the imaging device 110 or the object completes the positioning. Therefore, the operation time and/or user efforts may be reduced. The imaging operation may be fully automated.

In some embodiments, the imaging operation of the imaging device 110 may also be implemented by the user (e.g., a doctor or a technician). For example, the target imaging information of the imaging device 110 may be obtained together with the target device positioning information of the imaging device 110 in operation 520. The user may manually control the imaging device 110 to perform the imaging operation after the object and the imaging device 110 complete the positioning. As another example, the target imaging information may be the imaging parameters determined or adjusted by the user after the imaging device 110 and the object complete the positioning. After the user determines or adjusts the imaging parameters, the user may manually control the performance of the imaging operation to obtain the target image.

It should be noted that each of operations 510-550 may be automatically implemented by the imaging system to achieve full automation of the entire image acquisition process, thereby reducing labor costs and improving the accuracy and efficiency of the image acquisition. In some embodiments, the one or more of operations 510-550 may be automatically implemented by the imaging system, while the remaining operations may be implemented manually, which may not be limited in the present disclosure.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added.

In some embodiments, a computer-aided diagnosis system (CAD) may be installed in the imaging system. After the target image is input into the CAD, a result report may be output.

In some embodiments, the processing device 120 may also perform a feature recognition on the target image to generate a feature recognition result of the object, generate a result report based on the feature recognition result, and transmit the result report to one or more target client terminals. The one or more target client terminals refer to one or more terminals (e.g., the terminal 140) of one or more target clients. In some embodiments, the one or more target clients include the object and/or a doctor. In some embodiments, the feature recognition may be understood as a feature recognition performed on the target image based on a feature recognition algorithm. In some embodiments, the feature recognition result refers to a recognition result on the region of interest of the object in the target image. In some embodiments, the feature recognition result of the object may indicate whether there is an abnormality (e.g., lesions, etc.) in the region of interest of the object in the target image, and the result report may include an inspection result of the object automatically generated by the imaging system 100 based on the feature recognition result.

In some embodiments, the feature recognition result may be determined based on a result recognition model (e.g., a machine learning model). For instance, the target image may be input to a machine learning model, and the machine learning model may output a result including a feature recognition result. the target image may be input into a machine learning model, and the machine learning model may output a result of whether there is an abnormality (e.g., lesions, etc.) in the region of interest of the object in the target image. In some embodiments, the processing device 120 may also directly obtain the result report through the machine learning model. That is, the processing device 120 may input the target image into the machine learning model, and the output data of the machine learning model may include the result report. In some embodiments, the machine learning model may include a K-Nearest Neighbor (KNN) model, a Bayesian model, a Decision Tree model, a random forest model, a logarithmic probability Logistic regression model, a Neural Network (NN) model, an Ensemble Learning model, or the like, or any combination thereof.

In some embodiments, the one or more target terminals may be terminals (e.g., a mobile phone, etc.) of the object and the user. The imaging system may transmit the result report to the target terminal. The object may directly learn about the result report of the object. The user may make a further diagnosis for the object based on the result report. In some embodiments, the imaging system may transmit the result report to the target terminal using a short message or a network. The user or the object may view the result report through an application on the mobile phone.

Figure 6:
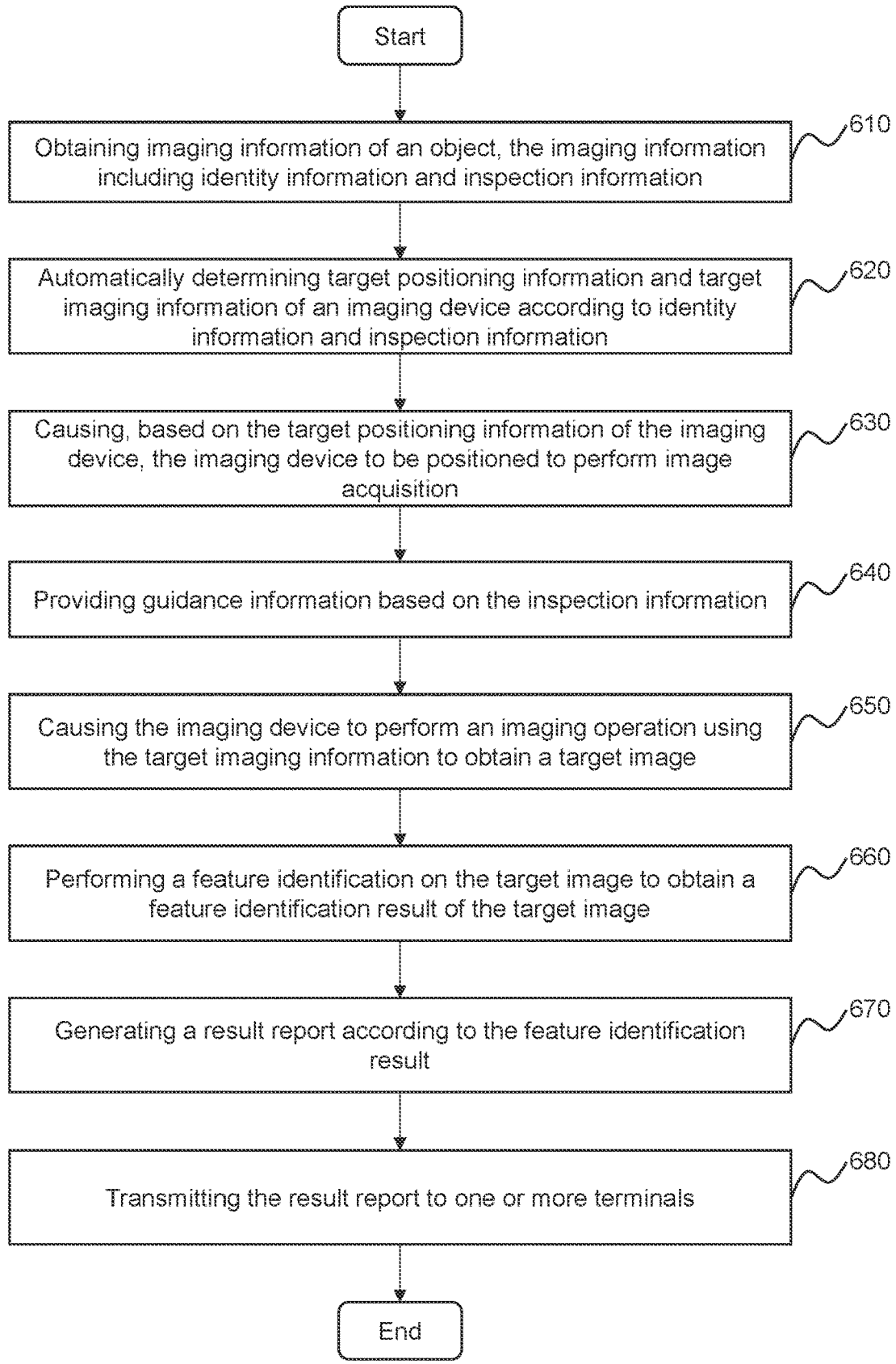
FIG. 6 is a logical schematic diagram illustrating a method for image acquisition according to some embodiments the present disclosure.

FIG. 6 is a logical schematic diagram illustrating a method for image acquisition according to some embodiments of the present disclosure. For illustration purposes, the present disclosure mainly describes the method relating to an X-ray imaging system. It should be noted that the X-ray imaging system described below is merely provided as an example, and not intended to limit the scope of the present disclosure. The methods disclosed herein may be applied to any other imaging systems. As shown in FIG. 6, the method for image acquisition may include the following operations. In 610, imaging information of an object may be obtained. The imaging information may include identity information and inspection information. As used herein, the identity information may include physical characteristic information and personal information. In 620, when the object enters an inspection room, and target device positioning information and target imaging information of the imaging device 110 may be automatically determined according to the identity information and the inspection information. In some embodiments, an identity of the object may be identified first according to the identity information of the object, and then the target device positioning information and the target imaging information of the imaging device 110 may be determined based on the identity information and the inspection information of the object. In 630, the processing device may cause, based on the target device positioning information of the imaging device 110, the imaging device 110 to be positioned to perform the image acquisition. In 640, guidance information may be provided based on the inspection information. The guidance information may be configured to guide positioning of the object. In 650, in response to completing the positioning of the imaging device 110 and the positioning of the object, the processing device 120 may cause the imaging device 110 to perform an imaging operation (e.g., an exposure operation) using the target imaging information to obtain a target image. In operations 660-670, in response to completing the imaging operation, the target image may be obtained, and the processing device 120 may perform a feature recognition on the target image to obtain a feature recognition result of the target image, and generate a result report according to the feature recognition result. In 680, the processing device 120 may transmit the result report to one or more terminals (e.g., one or more target client terminals) for reference by the object and a user (e.g., a doctor or an operator). More descriptions regarding operations 610-680 may be found in FIG. 5 and the descriptions thereof.

Through the automatic image acquisition and processing flow shown in FIG. 6, the imaging system 100 may cause the imaging device 110 to automatically position the object according to the identity information and inspection information of the object after the object enters the inspection room, and may automatically guide the positioning of the object. After the positioning is completed, the imaging system 100 may automatically perform the imaging operation, wherein the target imaging information corresponding to the imaging operation may be determined according to the identity information and inspection information of the object. In addition, the imaging system 100 may also automatically process and analyze the medical image obtained by the automatic imaging operation to generate the result report, and transmit the result report to the object or the user. Throughout the entire process, the processing device 120 may process data, and transmit instructions to cause the imaging device to perform related operations and guide the positioning of the object, thereby reducing manual operations by a user, improving the efficiency of the entire inspection process, and reducing or avoiding problems caused by human errors or cross-user variations.

Merely by way of example, in a medical imaging process using an X-ray imaging device (e.g., a suspended X-ray imaging device, a C-arm X-ray imaging device), a digital radiography (DR) device (e.g., a mobile digital X-ray imaging device), a CT device, a PET device, an MRI device, etc., before acquiring an image of the object, the imaging device 110 needs to set an imaging protocol corresponding to a region of interest of the object, so as to accurately and effectively obtain a target image of the object. In some embodiments, since there are many types of regions of interest (ROI), there may be many types of imaging protocols corresponding to different regions of interest. Therefore, a user (e.g., a doctor, an operator) may misuse and select a wrong imaging protocol. In some embodiments, it may also happen that the object is improperly positioned, resulting in imaging of an inaccurate region of interest. Either or both of the above situations may lead to incompatibility between the region of interest of the object and the imaging protocol during an actual imaging. In some embodiments, after the imaging device 110 completes imaging, it needs to perform an image processing on the acquired image data. An image processing algorithm used for the image processing may be compatible with or correspond to the region of interest of the object specified in the selected imaging protocol, and different positions may correspond to different image processing algorithms to ensure the accuracy of the image of the region of interest. If the imaging protocol does not match the region of interest that is actually imaged, the image processing algorithm may be incompatible with the ROI whose image is actually acquired (or referred to as an actual region of interest for brevity), which may result in relatively poor image quality of the processed image. Merely by way of example, the region of interest of the object specified in the selected imaging protocol is a palm in the left hand of a patient, on the basis of which target device positioning information, target patient positioning information, and a target image processing algorithm are determined; if the patient and/or the imaging device is improperly positioned, that is, the region of interest in the medical image actually imaged is not the palm in the left hand of the patient, the selected imaging protocol may not match the region of interest that is actually imaged. Therefore, the image processing algorithm corresponding to the selected imaging protocol may be incompatible with the ROI whose image is actually acquired, which may result in relatively poor image quality of the processed image.

In some embodiments of the present disclosure, after the imaging is completed and before the image is processed, it may be determined whether an imaged medical image is compatible with a current imaging protocol, and then determined whether to adjust a target image processing algorithm corresponding to the medical image based on a determination result to ensure compatibility between the target image processing algorithm and the region of interest represented in the medical image. If the target image processing algorithm that is compatible with the region of interest of the object in the medical image is used, a medical image of satisfactory quality may be generated.

Figure 7:
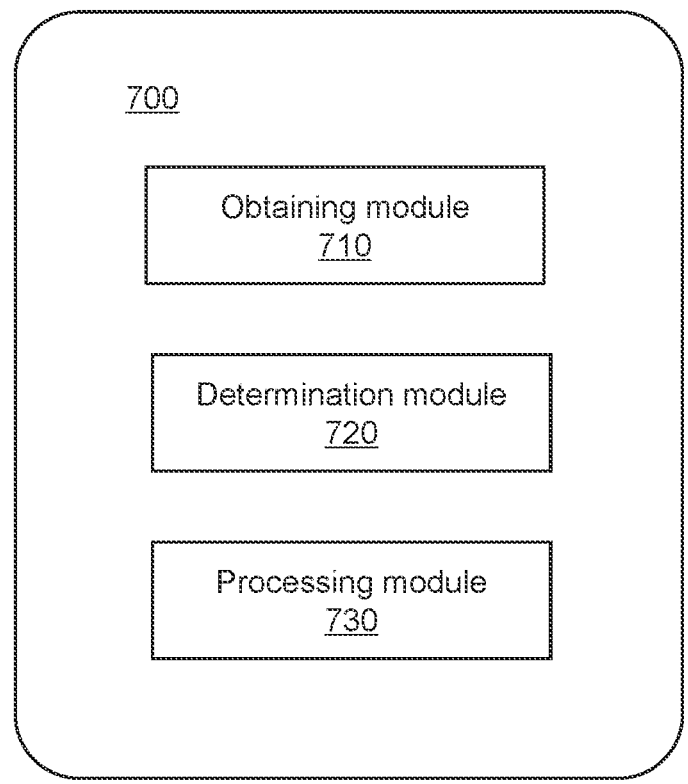
FIG. 7 is a block diagram illustrating an exemplary imaging system according to some embodiments the present disclosure.

FIG. 7 is a block diagram illustrating an exemplary configuration 700 of the processing device 120 imaging system according to some embodiments of the present disclosure. In some embodiments, processing device 120 may be implemented on a computing device 200 (e.g., the processor 210) illustrated in FIG. 2 or a CPU 340 as illustrated in FIG. 3. As illustrated in FIG. 7, the processing device 120 may include an obtaining module 710, a determination module 720, and a processing module 730. Each of the modules described above may be a hardware circuit that is designed to perform certain actions, e.g., according to a set of instructions stored in one or more storage media, and/or any combination of the hardware circuit and the one or more storage media.

The obtaining module 710 may be configured to obtain, using an imaging device (e.g., the imaging device 110), a medical image of an object acquired according to a current imaging protocol. The medical image may include a representation of a region of interest of the object. In some embodiments, the region of interest of the object may include positions such as a head, a chest, limbs, etc. In some embodiments, the current imaging protocol may be understood as the imaging protocol selected to guide a current imaging operation, that is, the imaging protocol selected to guide the acquisition of the medical image. In some embodiments, the imaging protocol may include a plurality of types of imaging protocols.

The determination module 720 may be configured to determine whether the medical image is compatible with the current imaging protocol. In some embodiments, to determine whether the medical image is compatible with the current imaging protocol, a representation of the region of interest of the object may be identified in the medical image, and then whether the medical image is compatible with the current imaging protocol may be determined by comparing the region of interest of the object in the current imaging protocol with the identified region of interest of the object in the medical image. In some embodiments, the determination module 720 may identify the region of interest of the object represented by the medical image through an image identification algorithm. In some embodiments, the image identification algorithm may include an image identification algorithm based on a convolutional neural network, an image identification algorithm based on image feature extraction (e.g., a SIFT algorithm, a SURF algorithm, etc.), etc. In some embodiments, if the representation of the region of interest of the object in the medical image is determined to correspond to the region of interest of the object specified in the current imaging protocol, the comparison result may be determined to include that the medical image is compatible with the current imaging protocol. If the representation of the region of interest of the object is determined not to correspond to the region of interest of the object specified in the current imaging protocol, the comparison result may be determined to include that the medical image is incompatible with the current imaging protocol. In some embodiments, the medical image may be directly compared with the current imaging protocol to obtain the comparison result without first processing the medical image to identify a representation of the ROI. In some embodiments, based on whether the medical image is compatible with the current imaging protocol, the determination module 720 may determine the target image processing algorithm of the medical image.

The processing module 730 may be configured to determine the target image processing algorithm by adjusting, based on the medical image, the current image processing algorithm that relates to the current imaging protocol. In some embodiments, the current image processing algorithm may correspond to the region of interest of the object specified in the current imaging protocol. The processing module 730 may process the medical image using the current image processing algorithm. In some embodiments, different regions of interest may correspond to different image processing algorithms. In some embodiments, the target image processing algorithm refers to an image processing algorithm that is configured to process the medical image. In some embodiments, when the medical image is found to be incompatible with the current imaging protocol, the processing module 730 may adjust the current image processing algorithm according to the medical image to determine the target image processing algorithm. In some embodiments, when the current image processing algorithm is adjusted, the corresponding target image processing algorithm may be determined based on the actual region of interest.

The processing module 730 may be further configured to designate the current image processing algorithm that relates to the current imaging protocol as the target image processing algorithm. In some embodiments, when the determination module 720 determines that the current imaging protocol is compatible with the medical image, the current image processing algorithm may not need to be adjusted, and the current imaging protocol may be directly used as the target image processing algorithm to process the medical image.

It should be noted that the above description is merely provided for the purposes of illustration, and not intended to limit the scope of the present disclosure. Apparently, for persons having ordinary skills in the art, multiple variations and modifications may be conducted under the teachings of the present disclosure. However, those variations and modifications do not depart from the scope of the present disclosure. For example, the determination module 720 and the guidance processing module 730 may be integrated into a single module. As another example, some other components/modules may be added into the processing device 120.

Figure 8:
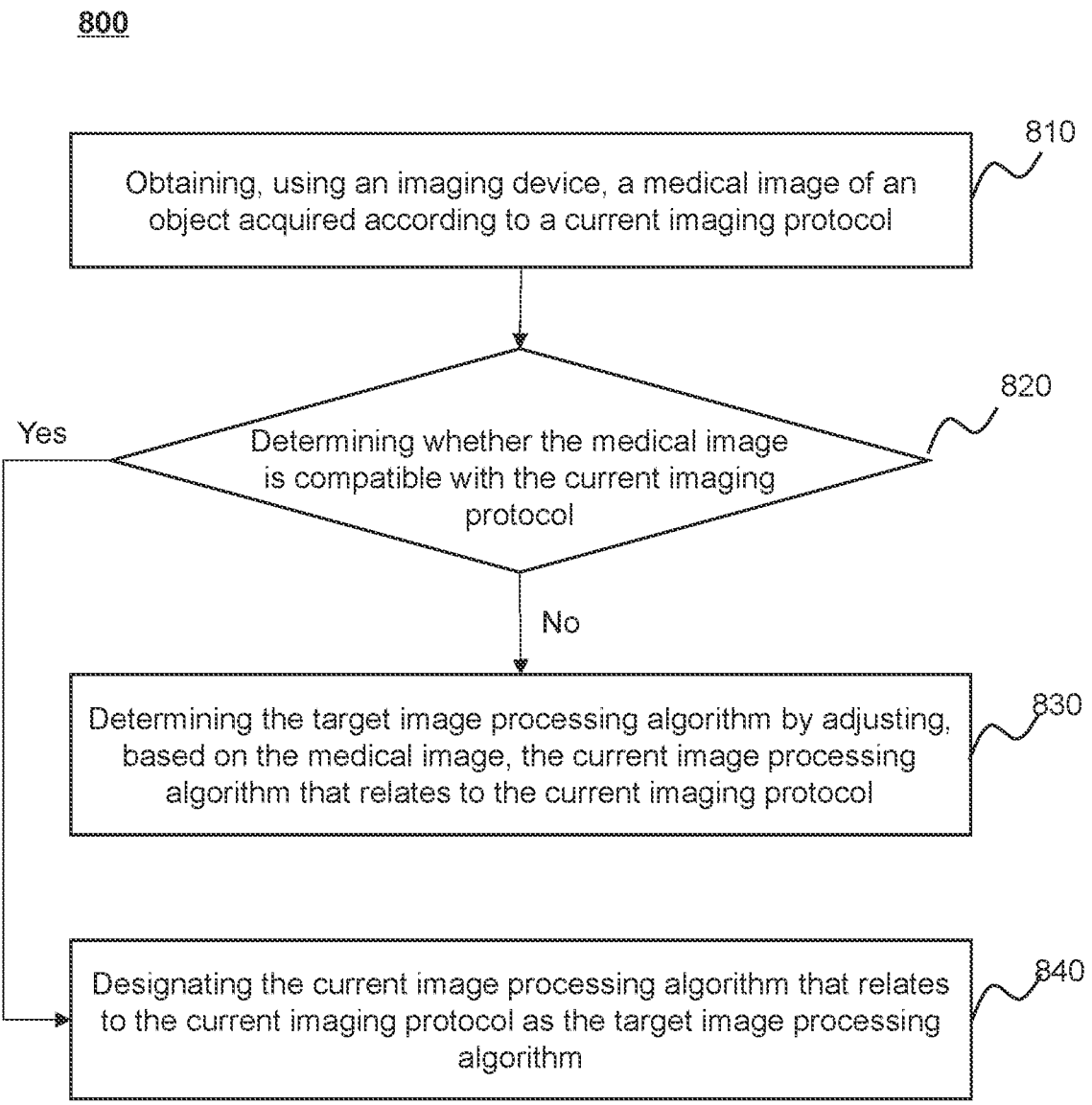
FIG. 8 is a flowchart illustrating an exemplary process for image processing according to some embodiments the present disclosure.

FIG. 8 is a flowchart illustrating an exemplary process for image processing according to some embodiments of the present disclosure. In some embodiments, process 800 may be implemented as a set of instructions (e.g., an application) stored in the storage device 130, storage device 220, or storage 390. The processing device 120, the processor 210, and/or the CPU 340 may execute the set of instructions, and when executing the instructions, the processing device 120, the processor 210, and/or the CPU 340 may be configured to perform the process 800. The operations of the illustrated process presented below are intended to be illustrative. In some embodiments, the process 800 may be accomplished with one or more additional operations not described and/or without one or more of the operations discussed. Additionally, the order of the operations of the process 800 illustrated in FIG. 8 and described below is not intended to be limiting.

In 810, the processing device 120 (e.g., the obtaining module 710) may obtain, using an imaging device (e.g., the imaging device 110), a medical image of an object acquired according to a current imaging protocol. The medical image may include a representation of a region of interest of the object.

In some embodiments, the imaging device 110 may include a CT device, a magnetic resonance device, a DR device, or the like. In some embodiments, the medical image of the object may be an image obtained by scanning or exposing the object by the imaging device 110. Therefore, the medical image may reflect a region of interest of the object. In some embodiments, the region of interest of the object may include positions such as a head, a chest, limbs, etc. In some embodiments, the current imaging protocol may be understood as the imaging protocol selected to guide a current imaging operation, that is, the imaging protocol selected to guide the acquisition of the medical image.

In some embodiments, the imaging protocol may include a plurality of types of imaging protocols. Different types of imaging protocols may correspond to different regions of interest. For example, the imaging protocol may include a head imaging protocol, a chest imaging protocol, an elbow joint imaging protocol, an ankle imaging protocol, etc. In some embodiments, the different imaging protocols may be paired with image processing algorithms. Accordingly, an image processing algorithm that corresponds to the region of interest of the object may be obtained.

In some embodiments, different types of imaging protocols, different types of image processing algorithms, and correspondence relationships between the different types of image processing algorithms and the different regions of interest may be pre-stored in the storage device 130. When the imaging device 110 performs an imaging operation, the user (e.g., a doctor, an operator, etc.) may obtain the current imaging protocol corresponding to a current imaging task from the storage device 130, and then the processing device 120 may cause the imaging device 110 to image the region of interest of the object according to the current imaging protocol to obtain the medical image of the object. In the subsequent image processing, if the image processing algorithm is not adjusted, the processing device 120 may perform the image processing on the medical image according to the current image processing algorithm. As used herein, a current image processing algorithm corresponds to a current imaging protocol that is configured to acquire image data of a region of interest.

In some embodiments, the acquisition of the current imaging protocol may not be obtained through a selection by the user, but be selected automatically by the imaging system 100 according to the current imaging task.

In some embodiments, after acquiring the medical image according to the current imaging protocol but before performing the subsequent image processing on the medical image, the processing device 120 may determine whether the medical image is compatible with the current imaging protocol in order to determine a target image processing algorithm. In response to determining that the medical image is compatible with the current imaging protocol, the current image processing algorithm corresponding to the current imaging protocol may be designated as the target image processing algorithm. In response to determining that the medical image is incompatible with the current imaging protocol, the current image processing algorithm may need to be adjusted to ensure the current image processing algorithm compatible with the region of interest of the object in the medical image. More descriptions regarding the determination may be found in operations 820-840 and the descriptions thereof.

In 820, the processing device 120 (e.g., the determination module 720) may determine whether the medical image is compatible with the current imaging protocol.

In some embodiments, to determine whether the medical image is compatible with the current imaging protocol, a representation of the region of interest of the object may be identified in the medical image, and then whether the medical image is compatible with the current imaging protocol may be determined by comparing the region of interest of the object in the current imaging protocol with the identified region of interest of the object in the medical image. In some embodiments, the processing device 120 may identify the region of interest of the object represented by the medical image through an image identification algorithm. In some embodiments, the image identification algorithm may include an image identification algorithm based on a convolutional neural network, an image identification algorithm based on image feature extraction (e.g., a SIFT algorithm, a SURF algorithm, etc.), etc. In some embodiments, a representation of the region of interest of the object in the medical image may be identified by image segmentation. More descriptions regarding the image segmentation may be found in FIG. 9 and the descriptions thereof.

In some embodiments, if the representation of the region of interest of the object in the medical image is determined to correspond to the region of interest of the object specified in the current imaging protocol the comparison result may be determined to include that the medical image is compatible with the current imaging protocol. If the representation of the region of interest of the object is determined not to correspond to the region of interest of the object specified in the current imaging protocol, the comparison result may be determined to include that the medical image is incompatible with the current imaging protocol.

In some embodiments, the ROI of an object to which an imaging protocol corresponds may be denoted using a keyword, a protocol tag, etc., in the imaging protocol. In some embodiments, the processing device 120 may determine the ROI to which the current imaging protocol corresponds by extracting the keyword, the protocol tag, etc., of the current imaging protocol. For example, the keyword extracted by the processing device 120 from the current imaging protocol is "head," the processing device 120 may determine that the current imaging protocol is a head imaging protocol. If the region of interest of the object is the head, the processing device 120 may determine that the current imaging protocol is compatible with the region of interest. As another example, if a protocol tag of the head imaging protocol is 001 and a protocol tag of a chest imaging protocol is 002, when the region of interest of the object is the head and the protocol tag extracted from the current imaging protocol is 002, the processing device 120 may determine that the region of interest of the object is incompatible with the current imaging protocol.

In some embodiments, the medical image may be directly compared with the current imaging protocol to obtain the comparison result without first processing the medical image to identify a representation of the ROI. For instance, a compatibility verification model (e.g., a machine learning model) may be used to determine whether the medical image is compatible with the region of interest represented in the medical image.

Merely by way of example, the processing device 120 may input the medical image and the current imaging protocol into the compatibility verification model. The compatibility verification model may output a matching result between the medical image and the current imaging protocol. In some embodiments, the matching result may include that the output medical image is compatible or incompatible with the current imaging protocol. In some embodiments, the matching result may also include a matching degree between the output medical image and the current imaging protocol, and the processing device 120 may further determine whether the output medical image is compatible or incompatible with the current imaging protocol according to the matching degree. For example, the processing device 120 may further determine whether the medical image of the object is compatible with the current imaging protocol based on whether the matching degree exceeds a matching threshold. If the matching degree is greater than or equal to the matching threshold, it may be determined that the medical image of the object is compatible with the current imaging protocol. If the matching degree is less than the matching threshold, it may be determined that the medical image of the object is incompatible with the current imaging protocol.

In some embodiments, the compatibility verification model may include a machine learning model. In some embodiments, the machine learning model may include a K-Nearest Neighbor (KNN) model, a Bayesian model, a Decision Tree model, a random forest model, a logarithm Probability regression (logistic regression) model, a neural network (NN) model, an ensemble learning model, or the like, or any combination thereof.

In some embodiments, the machine learning model may be obtained by training an initial machine learning model in the following manner. Training data may be acquired. The training data may include a plurality of historical medical images, and a plurality of historical imaging protocols corresponding to the plurality of historical medical images. In some embodiments, the matching relationship between a historical medical image and the corresponding historical imaging protocol may be empirically determined by one or more users, and a determination result (e.g., the historical medical image is compatible with the corresponding historical imaging protocol) may be labeled using a protocol tag, a keyword, etc. Then the plurality of historical medical images and the plurality of historical imaging protocols may be used as input data, and the determination result may be used as a reference standard. The input data and the reference standard may be input into the initial machine learning model for training to provide the trained machine learning model.

In some embodiments, based on whether the medical image is compatible with the current imaging protocol, the processing device 120 may determine the target image processing algorithm of the medical image. In some embodiments, in response to determining that the medical image is incompatible with the current imaging protocol, the processing device 120 may perform operation 830. In some embodiments, in response to determining that the medical image is compatible with the current imaging protocol, the processing device 120 may perform operation 840.

In 830, the processing device 120 (e.g., the processing module 730) may determine the target image processing algorithm by adjusting, based on the medical image, the current image processing algorithm that relates to the current imaging protocol.

In some embodiments, the current image processing algorithm may correspond to the region of interest of the object specified in the current imaging protocol. If the medical image is compatible with the current imaging protocol, it means that the region of interest of the object reflected in the medical image is compatible with the region of interest of the object in the current imaging protocol, so that the current image processing algorithm is compatible with the region of interest of the object reflected in the medical image. Therefore, the processing device 120 may process the medical image using the current image processing algorithm.

In some embodiments, different regions of interest may correspond to different image processing algorithms. For example, in a medical image of a hand, each finger may need to be identified, and in a medical image of the head, an outline of a skull may need to be identified. Since a size (e.g., a length, a width) of the fingers is different from a size of the skull, the corresponding image processing algorithms may provide different image resolutions.

In some embodiments, since the abilities of different regions of interest to absorb radiation may be different, if the current imaging protocol is incompatible with the actual region of interest, the acquired medical image may be of low quality due to, e.g., overexposure and/or insufficient exposure. For example, the current imaging protocol is for acquiring an image of the head of the object, and the actual region of interest of the object is the palm of the object; in an actual imaging process, an imaging dose of the head may be used to image the palm. Since the imaging dose of the head is greater than the imaging dose of the palm, the imaging dose of the actual region of interest of the object (i.e., the palm) may be too much, resulting in a medical image of low image quality. As another example, the current imaging protocol is for acquiring an image of the liver of the object, and the actual region of interest of the object acquired in the imaging operation is the lung; in an actual imaging process, an imaging dose of the liver is used to image the lung. Although a position of the liver is close to a position of the lung, parameters (e.g., thickness, component, etc.) of the lung may be different from those of the liver. Therefore, a desired imaging dose of the liver may be different from a desired imaging dose of the lung, resulting in a medical image of relatively low image quality. In the subsequent image processing, an appropriate image processing algorithm may be selected to improve the image quality including, e.g., resolution, the signal-to-noise ratio of the medical image, sharpness, or the like, or a combination thereof.

In some embodiments, the target image processing algorithm refers to an image processing algorithm that is configured to process the medical image. In some embodiments, the target image processing algorithm may correspond to the region of interest of the object reflected in the medical image, that is, the actual region of interest. In some embodiments, when the medical image is found to be incompatible with the current imaging protocol, the processing device 120 may adjust the current image processing algorithm according to the medical image to determine the target image processing algorithm. Therefore, the target image processing algorithm may be compatible with the actual region of interest represented in the medical image, thereby improving the image quality of the medical image. In some embodiments, when the current image processing algorithm is adjusted, the corresponding target image processing algorithm may be determined based on the actual region of interest. As used herein, the actual region of interest of the object may be determined based on the medical image. After the region of interest of the object is determined, the target image processing algorithm may be obtained from the storage device according to the corresponding relationship between the region of interest of the object and the image processing algorithm. More descriptions about determining the region of interest of the object may be found in FIG. 9 and the descriptions thereof.

In 840, the processing device 120 (e.g., the processing module 730) may designate the current image processing algorithm that relates to the current imaging protocol as the target image processing algorithm.

In some embodiments, when the processing device 120 determines that the current imaging protocol is compatible with the medical image, the current image processing algorithm may not need to be adjusted, and the current imaging protocol may be directly used as the target image processing algorithm to process the medical image.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, operation 810 and operation 820 may be combined into a single operation. As another example, one or more other optional operations (e.g., a storing operation) may be added elsewhere in the process 800. In the storing operation, the processing device 120 may store information and/or data (e.g., the medical image of the object, the image processing algorithm, the imaging protocol, etc.) associated with the imaging system 100 in a storage device (e.g., the storage device 130) disclosed elsewhere in the present.

Figure 9:
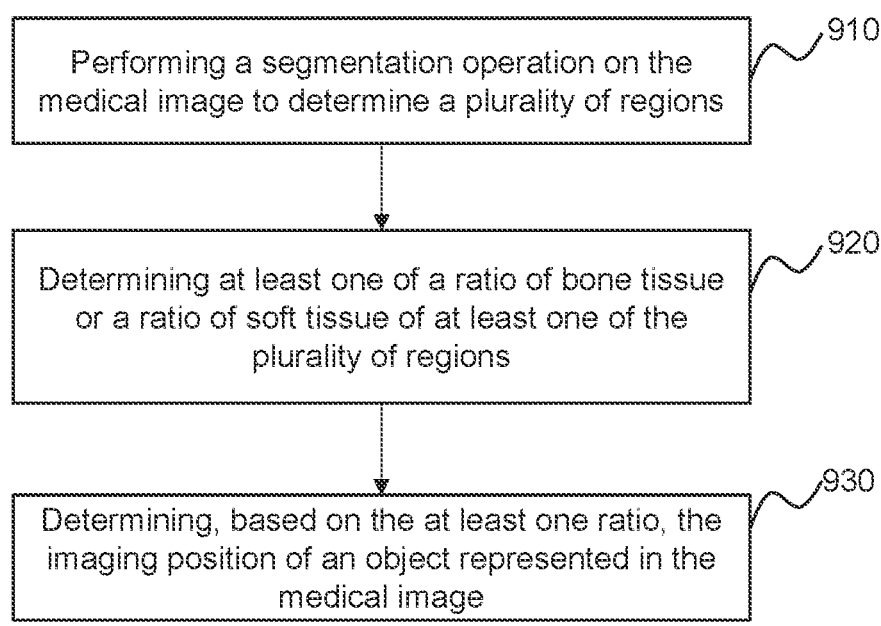
FIG. 9 is a flowchart illustrating an exemplary process for determining a region of interest of an object based on a medical image according to some embodiments of the present disclosure.

FIG. 9 is a flowchart illustrating an exemplary process for determining a region of interest of an object represented in a medical image according to some embodiments of the present disclosure. In some embodiments, process 900 may be implemented as a set of instructions (e.g., an application) stored in the storage device 130, storage device 220, or storage 390. The processing device 120, the processor 210, and/or the CPU 340 may execute the set of instructions, and when executing the instructions, the processing device 120, the processor 210, and/or the CPU 340 may be configured to perform the process 900. The operations of the illustrated process presented below are intended to be illustrative. In some embodiments, the process 900 may be accomplished with one or more additional operations not described and/or without one or more of the operations discussed. Additionally, the order of the operations of the process 900 illustrated in FIG. 9 and described below is not intended to be limiting. Operations 820 and 830 of FIG. 8 may be achieved according to the process 900.

In 910, the processing device 120 (e.g., the determination module 720) may perform a segmentation operation on the medical image to determine a plurality of regions.

In some embodiments, the segmentation of the medical image may be understood as dividing the medical image into a plurality of separate regions. The process for image segmentation may also regarded as a process for labeling. For example, pixels belonging to a same region may be assigned a same label and pixels belonging to different regions may be assigned different labels so as to distinguish different regions. In some embodiments, the segmentation operation may include segmenting the medical image into the plurality of regions based on a morphological template, an image segmentation algorithm, or the like, or any combination thereof.

In some embodiments, the processing device 120 may segment the medical image based on the morphological template. In some embodiments, the morphological template may be understood as a template configured according to anatomical characteristics of a human body. The human body may be roughly divided into a plurality of parts (e.g., the head, a trunk, a lung field, the limbs, etc.) corresponding to the morphological template. In some embodiments, after acquiring the medical image of the object, the processing device 120 may apply the morphological template to the medical image to segment the medical image into different regions. Based on a segmentation result, a region of interest in the medical image that includes a representation of and corresponds to a region of interest of the object may be determined. In some embodiments, segmentation using a morphological template may be suitable for segmenting an ROI in a medical image that corresponds to a region of a relatively large size of the object. For example, segmentation using a morphological template may be suitable for segmenting an ROI in a medical image that corresponds to a limb, the trunk, the head, the lung region, etc., of the object. In some embodiments, segmentation using a morphological template may be less suitable for segmenting an ROI in a medical image that corresponds to a region of a relatively small size of the object. For example, a segmentation result, an ROI identified in a medical image, obtained by way of segmentation using a morphological template may be unsuitable for determining whether the ROI identified in the image corresponds to an ankle joint or an outer region of a calf of the object.

In some embodiments, the processing device 120 may use the image segmentation algorithm to segment the medical image of the object to determine a plurality of regions in the medical image. In some embodiments, the image segmentation algorithm may include a threshold segmentation algorithm, a region segmentation algorithm, an edge segmentation algorithm, or the like.

In 920, the processing device 120 (e.g., the determination module 720) may determine at least one of a ratio of bone tissue or a ratio of soft tissue of at least one of the plurality of regions.

In some embodiments, the processing device 120 may determine the ratio of bone tissue in at least one of the plurality of regions through the image segmentation algorithm. Alternatively or additionally, the processing device 120 may determine the ratio of soft tissue in at least one of the plurality of regions through the image segmentation algorithm. In some embodiments, the processing device 120 may determine both the ratio of bone tissue and the ratio of soft tissue in at least one of the plurality of regions through the image segmentation algorithm. In some embodiments, the ratio of a tissue (e.g., bone tissue, soft tissue) of a region (e.g., an ROI) of an object may be estimated by determining a ratio of the area of the tissue in the corresponding region (e.g., the corresponding ROI) in the medical image to the area of the corresponding region (e.g., the corresponding ROI) in the medical image. The region in the medical image corresponding to the (physical) region of the object may be determined by segmenting the medical image according to the image segmentation algorithm. A tissue (e.g., bone tissue, soft tissue) in the region in the medical image may be identified based on imaging parameters, grayscale data, etc., of the medical image (or the region in the medical image). In some embodiments, the area of a region in a medical image may be determined based on the pixel count in the region and the dimension of a pixel in the region. Accordingly, a ratio of a tissue in a region may be determined based on the ratio of the pixel count of the tissue to the pixel count of the region. For brevity, a ratio of a tissue (e.g., bone tissue, soft tissue), or referred to as a tissue ratio, may be used in the context of a physical region (e.g., an ROI) of an object, or in the context of a corresponding region in a medical image that includes a representation of the physical region of the object.

In some embodiments, the imaging parameter of the region of interest of the object may include at least one of an imaging dose and grid information. As used herein, an imaging dose refers to a radiation dose employed in acquiring a medical image by the imaging device 110. In some embodiments, the grid information may include whether a grid is provided in the imaging device 110 and a filtering efficiency of the grid for filtering radiation. For example, the grid information may include that no grid is used in the imaging device 110 when imaging the object, or a portion thereof. As another example, the grid information may include that a grid is used in the imaging device 110 when imaging the object, or a portion thereof, and the filtering efficiency for radiation during the imaging of the object, or a portion thereof, is 20%, indicating that 20% of the radiation emitted by the imaging device 110 is filtered out and therefore the radiation dose is reduced by 20% than that emitted by the imaging device 110. In some embodiments, when the imaging device 110 is a DR device, the imaging parameter may also include a distance from the tube to the detector of the DR device.

The above one or more imaging parameters may reflect the radiation dose actually impinging on the object for imaging so as to reflect an overall amount of radiation actually used for imaging, which, in turn, relates to a reference grayscale value, e.g., the maximum grayscale value, of the medical image. In some embodiments, the medical image of the object may be a grayscale image. The imaging dose, the distance from the tube to the detector, and the grid information may each affect the grayscale values of pixels in the medical image. For example, by increasing the imaging dose, the grayscale values of pixels in the acquired medical image may be increased if other imaging parameters remain the same. As another example, by increasing the distance from the tube to the detector, the grayscale value of the medical image may be decreased if other imaging parameters remain the same. As still another example, if a grid is used in an imaging operation, the radiation dose may be decreased, and the grayscale value of the medical image may be lowered.

In some embodiments, when it is determined, based on the imaging parameters, that the grayscale value of the medical image is low, the processing device 120 may reduce the grayscale threshold value accordingly in the image segmentation algorithm, thereby improving the accuracy of the ratio of bone tissue or the ratio of soft tissue. In this way, the medical image may be finely segmented according to, e.g., the ratio of bone tissue and/or the ratio of soft tissue.

It should be understood that at least one of the ratio of bone tissue or the ratio of soft tissue may reflect characteristics of certain regions of the object, and different regions of interest may correspond to different ratios of bone tissue and/or different ratios of soft tissue. For example, the ratio of bone tissue in the lung region is relatively low, while the ratio of soft tissue is relatively high. As another example, the ratio of bone tissue in the spine is relatively high, while the ratio of soft tissue is relatively low. A region of an object (or a corresponding region in a medical image including a representation of the region of the object) may be identified based on at least one of the ratio of bone tissue or the ratio of soft tissue of the region. For example, a region may be determined to belong to a lumbar spine, the spine, a pelvic lung field, etc., based on the ratio of bone tissue and/or the ratio of soft tissue of the region.

In some embodiments, different regions may be segmented based on grayscale data of different pixels. For example, a plurality of pixels whose grayscale data are within a first grayscale range may be deemed to belong to a region, and a plurality of pixels whose grayscale data are within a second grayscale range may be deemed to belong to another region. The different regions may correspond to different bone tissue ratios and/or different soft tissue ratios.

In 930, the processing device 120 (e.g., the determination module 720) may determine, based on the at least one ratio, the region of interest of the object represented in the medical image.

In some embodiments, different parts of the object may be characterized by different characteristic features. A characteristic feature of a region may include the ratio of bone tissue, the ratio of soft tissue, and/or a combination of the ratio of bone tissue and the ratio of soft tissue of the region. The processing device 120 may identify the region of interest of the object represented in the medical image from a plurality of regions in the medical image by comparing a characteristic feature of each of at least one of the plurality of regions with a known characteristic feature of the ROI. If the characteristic feature of a region matches a known characteristic feature of an ROI of the object, the region may be determined as the region of interest of the object.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For instance, the process illustrated in FIG. 9 may be applied to a 3D medical image to determine an ROI of an object represented in the medical image.

Figure 10:
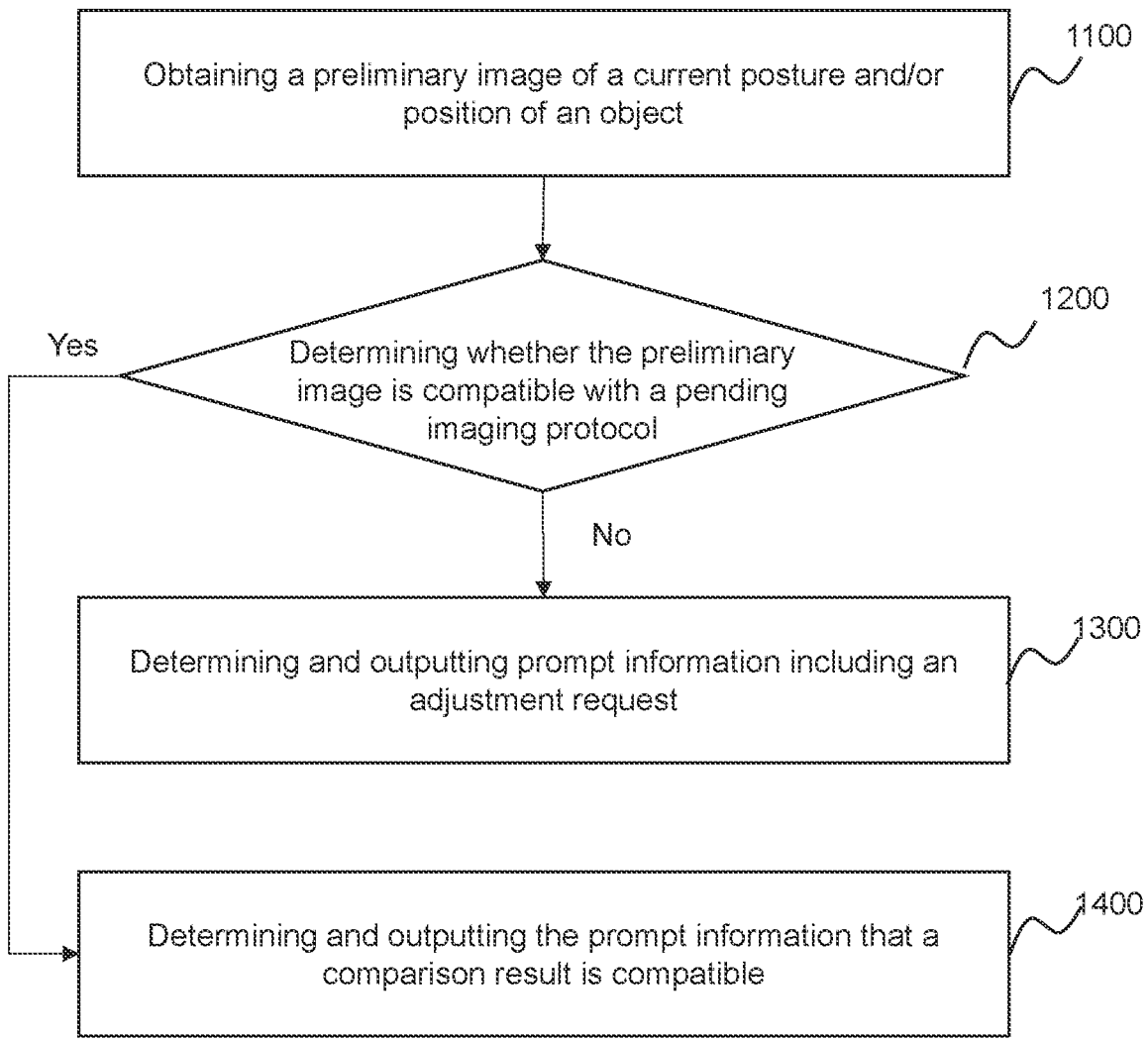
FIG. 10 is a flowchart illustrating an exemplary process for image acquisition and image processing according to some embodiments of the present disclosure.

FIG. 10 is a flowchart illustrating an exemplary process for image acquisition and image processing according to some embodiments of the present disclosure. In some embodiments, process 1000 may be implemented as a set of instructions (e.g., an application) stored in the storage device 130, storage device 220, or storage 390. The processing device 120, the processor 210, and/or the CPU 340 may execute the set of instructions, and when executing the instructions, the processing device 120, the processor 210, and/or the CPU 340 may be configured to perform the process 1000. The operations of the illustrated process presented below are intended to be illustrative. In some embodiments, the process 1000 may be accomplished with one or more additional operations not described and/or without one or more of the operations discussed. Additionally, the order of the operations of the process 1000 illustrated in FIG. 10 and described below is not intended to be limiting.

In 1100, the processing device 120 (e.g., the obtaining module 710) may obtain a preliminary image of a current posture and/or position of the object.

In some embodiments, the posture and/or the position of the object may be a posture and/or position of the object when performing the positioning, such as, lying down, standing, lying on a side, etc. In some embodiments, the preliminary image of the object may represent the posture and/or the position of the object. In some embodiments, the preliminary image may include an optical image or a non-visible light image. The non-visible light image may include, e.g., an infrared image. In some embodiments, the optical image refers to an image captured by a visible light camera, and the non-visible light image refers to an image captured by a non-visible light camera. For example, the infrared image may be an image captured by an infrared camera. Merely by way of example, the infrared camera may be installed on the imaging device 110 or other positions in the inspection room. After the object is positioned, the processing device 120 or a user (e.g., a doctor, an operator, etc.) may activate the infrared camera to obtain the preliminary image (the infrared image) of the object.

In 1200, the processing device 120 (e.g., the determination module 720) may determine whether the preliminary image is compatible with a pending imaging protocol.

In some embodiments, the pending imaging protocol may be an imaging protocol that has been set by the imaging device 110 before the preliminary image of the object is captured. For example, the pending imaging protocol may be an imaging protocol set by the imaging device 110 according to a default setting. The current imaging protocol refers to the imaging protocol adopted by the imaging device 110 for performing an imaging operation. In some embodiments, if during the imaging operation, the imaging protocol that has been set in the imaging device 110 (which can be regarded as the pending imaging protocol) is changed and the changed imaging protocol (which can be regarded as the current imaging protocol) is used to image the object, at this time, the pending imaging protocol may be incompatible with the current imaging protocol. In some embodiments, if during the imaging operation, the imaging protocol that has been set in the imaging device 110 is not changed and the imaging protocol is directly used to image the object, at this time, the pending imaging protocol may be compatible with the current imaging protocol.

In some embodiments, the determination as to whether the preliminary image is compatible with the pending imaging protocol may be achieved by determining whether the current posture and/or position of the object in the preliminary image is compatible with the pending imaging protocol. The current posture and/or position of the object may relate to the region of interest of the object for imaging. If the preliminary image is compatible with the pending imaging protocol, it means that the current posture of the object is compatible with the current imaging protocol. If the preliminary image is incompatible with the pending imaging protocol, it means that the current posture and/or position of the object is incompatible with the current imaging protocol.

In some embodiments, to determine whether the preliminary image is compatible with the pending imaging protocol, the preliminary image may be used to determine the region of interest of the object represented in the preliminary image. Subsequently, whether the preliminary image is compatible with the pending imaging protocol may be determined by comparing the region of interest of the object specified in the pending imaging protocol with the identified region of interest of the object represented in the preliminary image. In some embodiments, if the region of interest of the object represented in the preliminary image is determined to be compatible with the region of interest of the object specified in the pending imaging protocol, the processing device 120 may determine a comparison result that the preliminary image is compatible with the pending imaging protocol. If the region of interest of the object specified in the preliminary image is determined to be incompatible with the region of interest of the object specified in the pending imaging protocol, the processing device 120 may determine the comparison result that the preliminary image is incompatible with the pending imaging protocol.

In some embodiments, the processing device 120 may identify the region of interest of the object represented in the preliminary image through an image identification algorithm. In some embodiments, the image identification algorithm may include a machine learning model trained based on a convolutional neural network, an image recognition algorithm based on image feature extraction (e.g., a SIFT algorithm, a SURF algorithm, etc.), etc. In some embodiments, an image segmentation operation may be performed to determine the region of interest of the object represented in the preliminary image. More descriptions regarding the image segmentation manner may be found in FIG. 9 and the descriptions thereof, which may not be repeated herein.

In some embodiments, when a determination is made as to whether the region of interest of the object represented in the preliminary image is compatible with the pending imaging protocol, the processing device 120 may determine the ROI specified in the pending imaging protocol by extracting a keyword, a protocol tag, etc., of the pending imaging protocol. For example, the processing device 120 determines that the ROI specified in pending imaging protocol is "head" based on a keyword extracted from the pending imaging protocol; that is, the pending imaging protocol is a head imaging protocol. If the region of interest of the object represented in the preliminary image is determined to be the head of the object, the processing device 120 may determine that the pending imaging protocol is compatible with the region of interest represented in the preliminary image. As another example, if a protocol tag of the head imaging protocol is 001 and a protocol tag of a chest imaging protocol is 002, when the region of interest of the object represented in the preliminary image is determined to be the head and the protocol tag extracted from the pending imaging protocol is 002, the processing device 120 may determine that the region of interest of the object represented in the preliminary image is incompatible with the pending imaging protocol.

In some embodiments, the processing device 120 may directly compare the preliminary image with the pending imaging protocol to obtain the comparison result without first processing the preliminary image to identify a representation of the ROI of the object in the preliminary image. In some embodiments, the processing device 120 may determine whether the preliminary image is compatible with the pending imaging protocol through a machine learning model (e.g., a compatibility verification model). For instance, the processing device 120 may input the preliminary image and the pending imaging protocol into the compatibility verification model. The compatibility verification model may output a comparison result between the preliminary image and the pending imaging protocol. In some embodiments, the comparison result may include a conclusion that the ROI in the preliminary image is compatible or incompatible with the ROI specified in the pending imaging protocol (for brevity, referred to as the preliminary image being compatible or not with the pending imaging protocol). In some embodiments, the comparison result may include a matching degree between the preliminary image and the pending imaging protocol, and the processing device 120 may further determine whether the ROI in the preliminary image is compatible or incompatible with the ROI specified in the pending imaging protocol according to the matching degree. For example, the processing device 120 may determine whether the ROI in the preliminary image is compatible with the ROI specified in the pending imaging protocol based on whether the matching degree exceeds a matching degree threshold. If the matching degree is greater than or equal to the matching degree threshold, it may be determined that the preliminary image is compatible with the pending imaging protocol. If the matching degree is less than the matching degree threshold, it may be determined that the preliminary image is incompatible with the pending imaging protocol.

In some embodiments, the compatibility verification may include a machine learning model. In some embodiments, the machine learning model may include a K-Nearest Neighbor (KNN) model, a Bayesian model, a Decision Tree model, a random forest model, a logarithm Probability regression (logistic regression) model, a neural network (NN) model, an ensemble learning model, or the like, or any combination thereof.

In some embodiments, the machine learning model may be obtained by training an initial machine learning model in the following manner. Training data may be acquired. The training data may include a plurality of historical preliminary images, and a plurality of historical imaging protocols corresponding to the plurality of historical preliminary images. In some embodiments, the matching relationship between a historical preliminary image and the corresponding historical imaging protocol may be empirically determined by one or more users, and a determination result (e.g., the historical preliminary image being compatible with the corresponding historical imaging protocol or not) may be labeled using a protocol tag, a keyword, etc. Then the plurality of historical preliminary images and the plurality of historical imaging protocols may be used as input data, and the respective determination results may be used as corresponding target outputs. The input data and their respective target outputs may be used for training the initial machine learning model to provide the trained machine learning model.

In some embodiments, based on whether the preliminary image is compatible with the pending imaging protocol, the processing device 120 may determine prompt information. The prompt information may be used to inform the user whether the current posture and/or position of the object is compatible with the pending imaging protocol. In some embodiments, when it is determined that the preliminary image is incompatible with the pending imaging protocol, the processing device 120 may perform operation 1300. In some embodiments, when it is determined that the preliminary image is compatible with the pending imaging protocol, the processing device 120 may perform operation 1400.

In 1300, the processing device 120 (e.g., the processing module 730) may determine and output prompt information including an adjustment request.

In some embodiments, if the current posture of the object is incompatible with the pending imaging protocol, it may be that the pending imaging protocol is selected improperly, the current posture and/or position of the object is different from the posture specified by target patient positioning information of the object, or both the current posture and/or position of the object and the pending imaging protocol are improper. In some embodiments, when the processing device 120 determines that the preliminary image is incompatible with the pending imaging protocol, the processing device 120 may further determine whether the incompatibility is due to an improper pending imaging protocol and/or due to an improper current posture and/or position of the object, and accordingly determine at least one of the prompt information of the protocol adjustment request or the prompt information of the position adjustment request to the user. In some embodiments, the user may determine whether to adjust the pending imaging protocol or adjust the current posture and/or position of the object according to the prompt information.

In some embodiments, when the processing device 120 determines whether the incompatibility is due to an improper pending imaging protocol and/or due to an improper current posture and/or position of the object, the processing device 120 may also determine an adjusted imaging protocol, an adjusted posture, and/or an adjusted position. In some embodiments, the adjusted imaging protocol, the adjusted posture, and/or the adjusted position may be used directly for further imaging and/or image processing without user intervention. In some embodiments, the adjusted imaging protocol, the adjusted posture, and/or the adjusted position may be provided to the user; the user may accept, reject, or further adjust the adjusted imaging protocol, the adjusted posture, and/or the adjusted position before application in guiding further imaging and/or image processing.

In some embodiments, when the processing device 120 determines that the preliminary image is incompatible with the pending imaging protocol, the processing device 120 may generate prompt information informing the user about the incompatibility without information regarding the cause for the incompatibility. The user may determine the cause of the incompatibility and adjustment needed, e.g., that the imaging protocol, the current posture, and/or the current position needs to be adjusted. An adjustment operation may be performed manually. For example, the user may manually adjust the imaging protocol, readjust the current posture, and/or readjust the current position in response to the prompt information. The adjustment operation may also involve the processing device 120 or other positioning devices. For example, the processing device 120 may determine corresponding guidance information according to the posture adjustment and/or the position adjustment the user determines, and the object may be caused to adjust the current posture and/or position according to the guidance information. Alternatively, the positioning device may cause the object to adjust the current posture and/or position of the object according to the guidance information. More descriptions regarding the guidance information may be found in operation 540 in FIG. 5 and the descriptions thereof.

In some embodiments, the imaging operation may be directly performed after the imaging protocol, the current posture, and/or the current position of the object is adjusted to obtain the corresponding medical image. The imaging operation may be initiated manually by the user. Alternatively, the processing device 120 may cause the imaging device 110 to perform the imaging operation automatically. In some embodiments, the processing device 120 may also analyze the preliminary image and the pending imaging protocol in real time. When determining that the preliminary image is compatible with the pending imaging protocol, the processing device 120 may initiate the imaging operation. More details may be found in operation 1400 and the descriptions thereof.

In 1400, the processing device 120 (e.g., the processing module 730) may determine and output the prompt information that the comparison result is compatible.

In some embodiments, when it is determined that the preliminary image and the pending imaging protocol is compatible, indicating that the current posture of the object is compatible with the pending imaging protocol, the processing device 120 may determine and output the prompt information informing the user of the comparison result. For example, the prompt information may include a message that the current posture and/or position of the object is compatible with the pending imaging protocol, and the imaging operation may be initiated to obtain the medical image.

In some embodiments, after the prompt information indicating that the comparison result is compatible is provided to the user, the user may initiate the imaging operation to obtain a medical image. In some embodiments, a control instruction may be issued automatically by the processing device 120 to cause the imaging device 110 to perform the imaging operation and obtain the medical image. Alternatively, the processing device 120 may issue the control instruction to the imaging device 110 according to the selected input information of the user. Therefore, the imaging device 110 may perform the imaging operation to obtain the medical image.

In some embodiments, by obtaining and analyzing a preliminary image of the object before the imaging device 110 acquires a medical image of the object, an imaging operation is to be performed only after it is determined that the pending imaging protocol or an adjusted imaging protocol is suitable for imaging the region of interest of the object, thereby obviating the need to adjust the image processing algorithm after imaging has been finished and/or avoiding the acquisition of an unacceptable medical image of the object.

It should be noted that the above description is merely provided for illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added.

It should be noted that different embodiments may produce different beneficial effects. In different embodiments, the possible beneficial effects may be any one or a combination of the above, or any other beneficial effects that may be obtained.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python, or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for automated image acquisition implemented on a computing device having one or more processors and one or more storage devices, comprising:
obtaining imaging information of an object, the imaging information including identity information and inspection information;
determining, based on the identity information and the inspection information, at least target device positioning information of an imaging device;
causing, based on the target device positioning information of the imaging device, the imaging device to be positioned to perform the image acquisition;
providing, based on the inspection information, guidance information, including:
generating a positioning reference image according to the inspection information, the positioning reference image reflecting a target position or posture of the object; and
determining the guidance information according to current patient positioning information of the object and the positioning reference image, the guidance information being configured to guide positioning of the object, the positioning of the object including adjusting a posture of the object to get ready to be imaged using the imaging device; and
obtaining a target image from an imaging operation by the imaging device, including:
obtaining, using the imaging device, a medical image of the object acquired according to a current imaging protocol, the medical image including a representation of a region of interest of the object;
inputting the medical image and the current imaging protocol into a compatibility verification model;
determining, based on an output of the compatibility verification model, whether the medical image is compatible with the current imaging protocol; and
in response to determining whether the medical image is compatible with the current imaging protocol, determining a target image processing algorithm of the medical image for generating the target image based on the medical image.

2. The method of claim 1, wherein
the determining, based on the identity information and the inspection information, at least target device positioning information of an imaging device includes: determining, based on the identity information and the inspection information, the target device positioning information and target imaging information of the imaging device, the target imaging information including target exposure information; and
the obtaining a target image from an imaging operation of the imaging device includes: in response to completing the positioning of the object, causing the imaging device to perform an exposure operation according to the target exposure information.

3. The method of claim 1, wherein the causing, based on the target device positioning information of the imaging device, the imaging device to be positioned to perform the image acquisition includes:
generating, based on the target device positioning information of the imaging device, a control instruction of the imaging device; and
causing the imaging device to be positioned according to the control instruction.

4. The method of claim 1, further including:
performing a feature recognition on the target image to generate a feature recognition result of the object;
generating, based on the feature recognition result, a result report; and transmitting the result report to one or more target client terminals.

5. The method of claim 1, wherein the determining, in response to determining whether the medical image is compatible with the current imaging protocol, a target image processing algorithm of the medical image includes:
in response to determining that the medical image is compatible with the current imaging protocol, designating a current image processing algorithm that relates to the current imaging protocol as the target image processing algorithm.

6. The method of claim 1, wherein the compatibility verification model is a machine learning model.

7. The method of claim 1, wherein the imaging device includes at least one of a computed tomography device, a magnetic resonance device, and a digital radiography device.

8. The method of claim 1, wherein the generating a positioning reference image according to the inspection information includes:
determining, based on the target device positioning information of the imaging device and the inspection information, target patient positioning information of the object; and
generating the positioning reference image according to the target patient positioning information of the object.

9. The method of claim 8, further comprising:
comparing the current patient positioning information of the object with the target patient positioning information of the object; and
determining, based on a comparison result between the current patient positioning information of the object and the target patient positioning information of the object, the guidance information.

10. The method of claim 8, wherein the determining the guidance information according to current patient positioning information of the object and the positioning reference image includes:
comparing the current patient positioning information of the object with the positioning reference image; and
determining, based on a comparison result between the current patient positioning information of the object and the positioning reference image, the guidance information.

11. The method of claim 1, wherein the determining, in response to determining whether the medical image is compatible with the current imaging protocol, a target image processing algorithm of the medical image includes:
in response to determining that the medical image is incompatible with the current imaging protocol, determining the target image processing algorithm by adjusting, based on the medical image, a current image processing algorithm that relates to the current imaging protocol.

12. The method of claim 11, further including:
obtaining a preliminary image of a current posture of the object;
determining whether the preliminary image is compatible with a pending imaging protocol; and
in response to determining whether the preliminary image is compatible with the current imaging protocol, determining a prompt.

13. The method of claim 12, wherein in response to determining whether the preliminary image is compatible with the current imaging protocol, the determining a prompt includes:

in response to determining that the preliminary image is incompatible with the current imaging protocol, the prompt including a request for a protocol adjustment or a request for a position adjustment.

14. The method of claim 12, wherein the preliminary image includes an optical image or an infrared image.

15. The method of claim 1, further comprising:
determining, based on the medical image, the region of interest of the object; and
determining whether the region of interest of the object is compatible with the current imaging protocol.

16. The method of claim 15, wherein the determining, based on the medical image, the region of interest of the object includes:
performing a segmentation operation on the medical image to determine a plurality of regions; and
determining, based on the plurality of regions, the region of interest of the object.

17. The method of claim 16, wherein the determining, based on the plurality of regions, the region of interest of the object includes:
determining at least one of a ratio of bone tissue or a ratio of soft tissue of at least one of the plurality of regions; and
determining, based on the at least one ratio, the region of interest of the object.

18. The method of claim 17, wherein the determining at least one of a ratio of bone tissue or a ratio of soft tissue of at least one of the plurality of regions includes:
obtaining grayscale data of at least one pixel of the at least one region and an imaging parameter of the current imaging protocol, and
determining, based on the grayscale data of the at least one pixel and the imaging parameter, the at least one ratio of the at least one region.

19. The method of claim 18, wherein the imaging parameter includes at least one of an imaging dose employed in acquiring the medical image, a distance from a tube to a detector of the imaging device, or grid information of the imaging device.

20. A system for automated image acquisition, including:
at least one storage device including a set of instructions; and
at least one processor configured to communicate with the at least one storage device, wherein when executing the set of instructions, the at least one processor is configured to direct the system to perform operations including:
obtaining imaging information of an object, the imaging information including identity information and inspection information;
determining, based on the identity information and the inspection information, at least target device positioning information of an imaging device, and cause, based on the target device positioning information of the imaging device, the imaging device to be positioned to perform the image acquisition;
providing, based on the inspection information, guidance information, including:
generating a positioning reference image according to the inspection information, the positioning reference image reflecting a target position or posture of the object; and
determining the guidance information according to current patient positioning information of the object and the positioning reference image, the guidance information being configured to guide positioning of the object, the positioning of the object including adjusting a posture of the object to get ready to be imaged using the imaging device; and obtaining a target image from an imaging operation by the imaging device, including:

obtaining, using the imaging device, a medical image of the object acquired according to a current imaging protocol, the medical image including a representation of a region of interest of the object;

inputting the medical image and the current imaging protocol into a compatibility verification model;

determining, based on an output of the compatibility verification model, whether the medical image is compatible with the current imaging protocol; and in response to determining whether the medical image is compatible with the current imaging protocol, determining a target image processing algorithm of the medical image for generating the target image based on the medical image.

* * * * *